(12) United States Patent
Gutowski et al.

(10) Patent No.: US 11,897,437 B2
(45) Date of Patent: Feb. 13, 2024

(54) METHOD AND SYSTEM FOR A VEHICLE SANITIZING MODE

(71) Applicant: Ford Global Technologies, LLC, Dearborn, MI (US)

(72) Inventors: Alan Gutowski, Wixom, MI (US); Curtis Jones, Wixom, MI (US); Fred Koberstein, Troy, MI (US); Stephen White, Saline, MI (US); Peter Mitchell Lyon, Brighton, MI (US); John Rollinger, Troy, MI (US); Scott Thompson, Belleville, MI (US); M. Scott Christensen, Canton, MI (US); David Hancock, Flat Rock, MI (US); Adam Richards, Royal Oak, MI (US); Steve Skikun, Commerce Charter Township, MI (US); Frank Fusco, Plymouth, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 610 days.

(21) Appl. No.: 17/073,592

(22) Filed: Oct. 19, 2020

(65) Prior Publication Data

US 2022/0118952 A1    Apr. 21, 2022

(51) Int. Cl.
*B60S 1/64* (2006.01)
*A61L 2/06* (2006.01)
(Continued)

(52) U.S. Cl.
CPC . *B60S 1/64* (2013.01); *A61L 2/06* (2013.01); *A61L 2/10* (2013.01); *A61L 2/24* (2013.01);
(Continued)

(58) Field of Classification Search
CPC ...... B60S 1/64; A61L 2/06; A61L 2/10; A61L 2/24; A61L 2202/11; A61L 2202/14;
(Continued)

(56) References Cited

U.S. PATENT DOCUMENTS 9,364,573 B2 * 6/2016 Deshays ................. G01J 1/429
10,391,527 B2    8/2019 Boin et al.
(Continued)

FOREIGN PATENT DOCUMENTS

JP    55119515 A * 9/1980 ............... B60H 1/02

OTHER PUBLICATIONS

English Translation of JP 55119515 A Description Espacenet (1980).*
(Continued)

*Primary Examiner* — Dale W Hilgendorf
(74) *Attorney, Agent, or Firm* — Vichit Chea; McCoy Russell LLP

(57) ABSTRACT

Methods and systems are provided for heat sanitizing a vehicle. In one example, a method may include, responsive to receiving a request for sanitization of a vehicle interior, activating an ultraviolet germicidal irradiation (UVGI) system and operating a heating, ventilation, and air-conditioning (HVAC) system to heat the vehicle interior above an upper threshold temperature for a threshold duration. In this way, the HVAC system may be advantageously used to expose the vehicle interior to temperatures that kill or inactive microbes while the UVGI system may supplement the heat sanitizing.

18 Claims, 12 Drawing Sheets

(51) Int. Cl.
*A61L 2/24* (2006.01)
*B60H 3/06* (2006.01)
*B60W 10/30* (2006.01)
*B60W 30/00* (2006.01)
*B60W 10/06* (2006.01)
*B60W 10/08* (2006.01)
*A61L 2/10* (2006.01)
*A61L 9/20* (2006.01)
*F24F 8/22* (2021.01)

(52) U.S. Cl.
CPC ............... *A61L 9/20* (2013.01); *B60H 3/06* (2013.01); *B60W 10/06* (2013.01); *B60W 10/08* (2013.01); *B60W 10/30* (2013.01); *B60W 30/00* (2013.01); *A61L 2202/11* (2013.01); *A61L 2202/14* (2013.01); *A61L 2202/25* (2013.01); *B60W 2520/04* (2013.01); *B60W 2530/00* (2013.01); *B60W 2540/00* (2013.01); *B60W 2710/065* (2013.01); *B60W 2710/08* (2013.01); *B60W 2710/305* (2013.01); *F24F 8/22* (2021.01)

(58) Field of Classification Search
CPC ........... A61L 2202/25; A61L 2209/111; A61L 2209/16; A61L 9/20; B60H 3/06; B60H 3/0078; B60H 1/00878; B60W 10/06; B60W 10/08; B60W 10/30; B60W 30/00; B60W 2520/04; B60W 2530/00; B60W 2540/00; B60W 2710/065; B60W 2710/08; B60W 2710/305; B60W 2710/083; B60W 50/14; B60W 2540/215; B60W 2710/182; B60W 10/18; B60W 20/15; F24F 8/22; B60K 6/48
See application file for complete search history.

(56) References Cited

U.S. PATENT DOCUMENTS

| | | | |
|---|---|---|---|
| 10,987,440 B1* | 4/2021 | Sood | H05B 47/115 |
| 11,135,333 B1* | 10/2021 | Sood | A61L 2/28 |
| 11,673,535 B2* | 6/2023 | Gutowski | B60S 1/64 |
| | | | 701/48 |
| 2009/0276130 A1* | 11/2009 | Whitney | B60H 1/322 |
| | | | 701/68 |
| 2012/0234930 A1* | 9/2012 | Wijaya | H04Q 9/00 |
| | | | 236/51 |
| 2014/0341777 A1* | 11/2014 | Deshays | G01K 13/00 |
| | | | 250/354.1 |
| 2018/0001736 A1* | 1/2018 | Kim | B60H 1/00878 |
| 2018/0229694 A1* | 8/2018 | Salter | B60J 7/043 |
| 2019/0091738 A1* | 3/2019 | Chen | B60H 1/00742 |
| 2019/0118613 A1* | 4/2019 | Ragazzi | B60H 1/004 |
| 2021/0308300 A1* | 10/2021 | Rathi | A61L 2/04 |
| 2021/0347265 A1* | 11/2021 | Park | B60K 11/02 |
| 2021/0380281 A1* | 12/2021 | Gurvich | A61L 2/04 |
| 2022/0055447 A1* | 2/2022 | Van Wiemeersch | A61L 2/04 |
| 2022/0118822 A1* | 4/2022 | Gutowski | B60H 1/00021 |
| 2022/0118951 A1* | 4/2022 | Gutowski | B60H 1/2225 |
| 2022/0153084 A1* | 5/2022 | Pecchia | B60H 3/0078 |
| 2022/0170653 A1* | 6/2022 | Green | F24F 11/30 |

OTHER PUBLICATIONS

Gutowski, A. et al., "Method and System for a Vehicle Sanitizing Mode," U.S. Appl. No. 16/864,751, filed May 1, 2020, 75 pages.
Gutowski, A. et al., "Method and System for a Vehicle Sanitizing Mode," U.S. Appl. No. 17/073,587, filed Oct. 19, 2020, 103 pages.
Gutowski, A. et al., "Method and System for a Vehicle Sanitizing Mode," U.S. Appl. No. 17/073,595, filed Oct. 19, 2020, 102 pages.

* cited by examiner

METHOD AND SYSTEM FOR A VEHICLE SANITIZING MODE

FIELD

The present description relates generally to methods and systems for a climate control system of a vehicle.

BACKGROUND/SUMMARY

Some pathogens, such as bacteria and viruses, can survive on plastic and metal vehicle surfaces for extended periods of time, leading to spreading or transmission to a human. Chemical sanitizers may be used to disinfect (e.g., decontaminate) the surfaces in a process known as chemical sanitization. For example, a person performing the chemical sanitization may spray or wipe the chemical sanitizer onto the vehicle surfaces. However, using chemical sanitizers may be time consuming, expensive, and resource exhausting. Further, it may be difficult to fully clean every vehicle surface using chemical sanitizers. For example, it may be difficult for the person to reach between seats and into crevices. As another example, disinfecting vehicle surfaces via chemical sanitizers may be physically demanding, and thus, some vehicle customers may be unable to perform the chemical sanitization. As still another example, chemical sanitizers have a specified contact time for killing and/or deactivating the pathogens, and if the person does not adhere to the specified contact time, the sanitization may be ineffective.

The inventors herein have recognized that many pathogens are heat-sensitive and can thus be killed or deactivated using heat sanitization. Further, the inventors herein have advantageously recognized that a heating, ventilation, and air-conditioning (HVAC) system may be operated to generate on-demand heat and that this may be combined with ultraviolet light (UV)-based sanitization for thorough vehicle cleaning.

In one example, the issues described above may be addressed by a method, comprising: responsive to receiving a request for cleaning an interior of a vehicle, activating an ultraviolet germicidal irradiation (UVGI) system and operating a heating, ventilation, and air-conditioning (HVAC) system to heat the interior above an upper threshold temperature for a first threshold duration. In this way, surfaces of the vehicle interior may be effectively decontaminated using systems already included in the vehicle and without chemical sanitizers or physical effort from a user.

As one example, the UVGI system may include a plurality of short-wavelength ultraviolet (UV) light sources directed at a plurality of surfaces of the interior of the vehicle, and activating the UVGI system may include emitting light from the UV light sources. As another example, operating the HVAC system to heat the interior above the upper threshold temperature for the first threshold duration may include flowing hot air from the HVAC system to the interior. The hot air may have a much greater temperature than that used for climate control (e.g., for passenger comfort). For example, operating the HVAC system to heat the interior above the upper threshold temperature for the first threshold duration may include operating in a vehicle sanitizing mode, the vehicle sanitizing mode including instructions for HVAC system settings that will heat the interior above the upper threshold temperature and maintain the interior above the upper threshold temperature for the first threshold duration. As another example, the vehicle sanitizing mode may include entry conditions, and thus, activating the UVGI system and operating the HVAC system to heat the interior above the upper threshold temperature for the first threshold duration may be further responsive to the entry conditions being met. For example, the entry conditions may include an indication the vehicle is unoccupied, an indication the vehicle is parked, and an indication vehicle doors and windows are closed. Further, responsive to a temperature of the interior being above the upper threshold temperature for the first threshold duration, the HVAC system may be operated to gradually reduce the temperature of the interior until one of a lower threshold temperature and a second threshold duration is reached.

As another example, the HVAC system may include a blower configured to generate air flow through the HVAC system, a heating component configured to receive the air flow from the blower, and delivery ducting fluidically coupling the heating component to the interior. Operating the HVAC system to heat the vehicle interior above the upper threshold temperature for the threshold duration may include operating the blower at maximum speed, generating hot air at the heating component, and flowing the hot air from the heating component to the vehicle interior via the delivery ducting. The heating component may be a heat exchanger configured to transfer heat from engine coolant to the hot air or may be an electric heater, such as a positive temperature coefficient heater, for example. Further, in some examples, in order to increase the heat transferred from the engine coolant to the hot air, a temperature of the engine coolant may be increased by increasing an idle speed set-point of the engine and turning off an engine cooling fan.

In this way, the interior of the vehicle may be decontaminated via hot air supplied from the HVAC system and light emitted by the UVGI system. The hot air may easily flow into hard-to-reach areas, such as between seats and in crevices, to provide effective sanitization throughout the interior of the vehicle. Further, the vehicle surfaces may be disinfected without physical effort from a human. By maintaining the temperature of the interior above the upper threshold temperature for the first threshold duration, non-observance of contact times may be avoided. As a result, the vehicle interior may be more thoroughly decontaminated than when chemical sanitizers are used, and pathogen transmission may be reduced.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
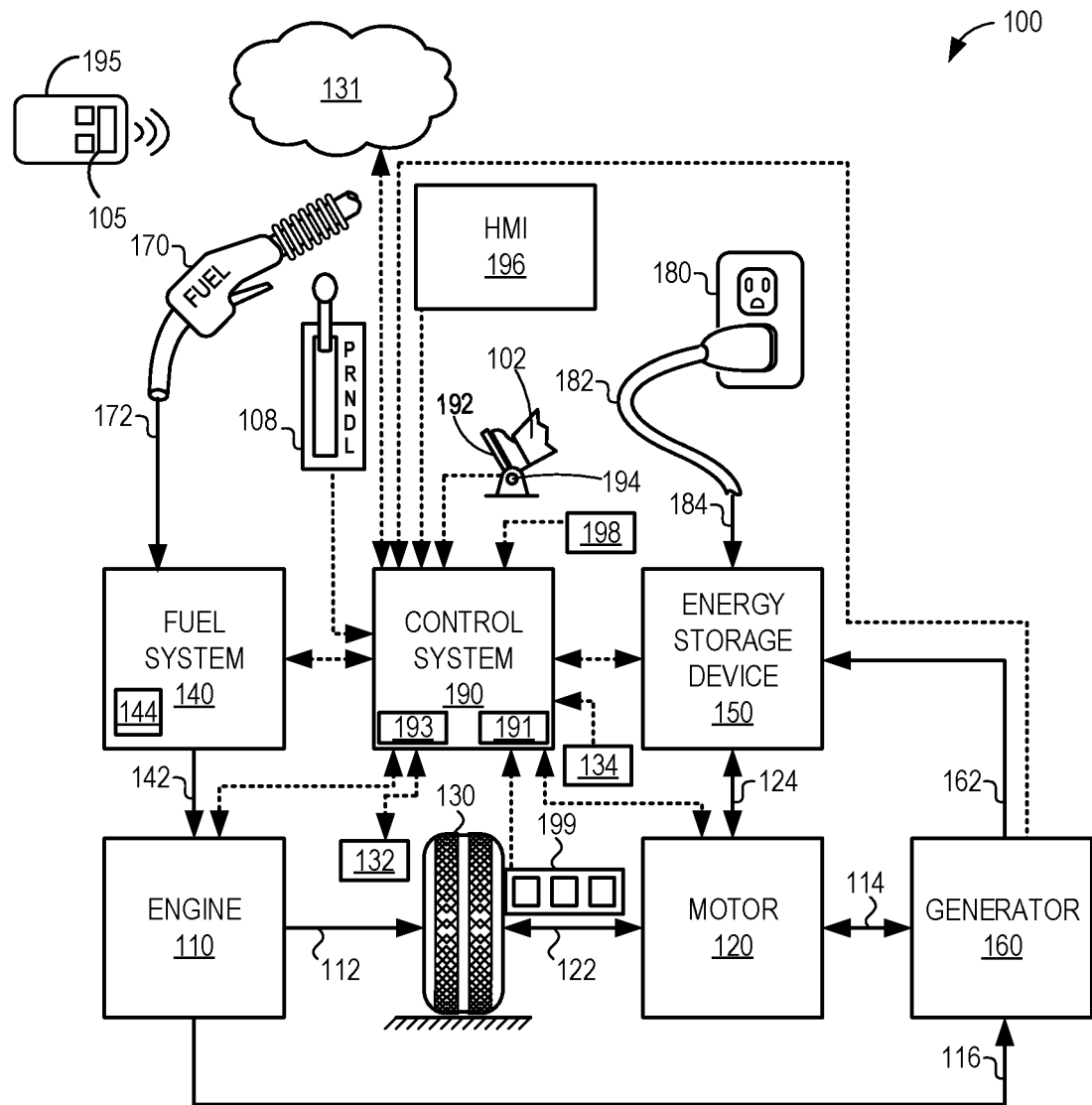
FIG. 1 schematically shows an example vehicle propulsion system.
Figure 2:
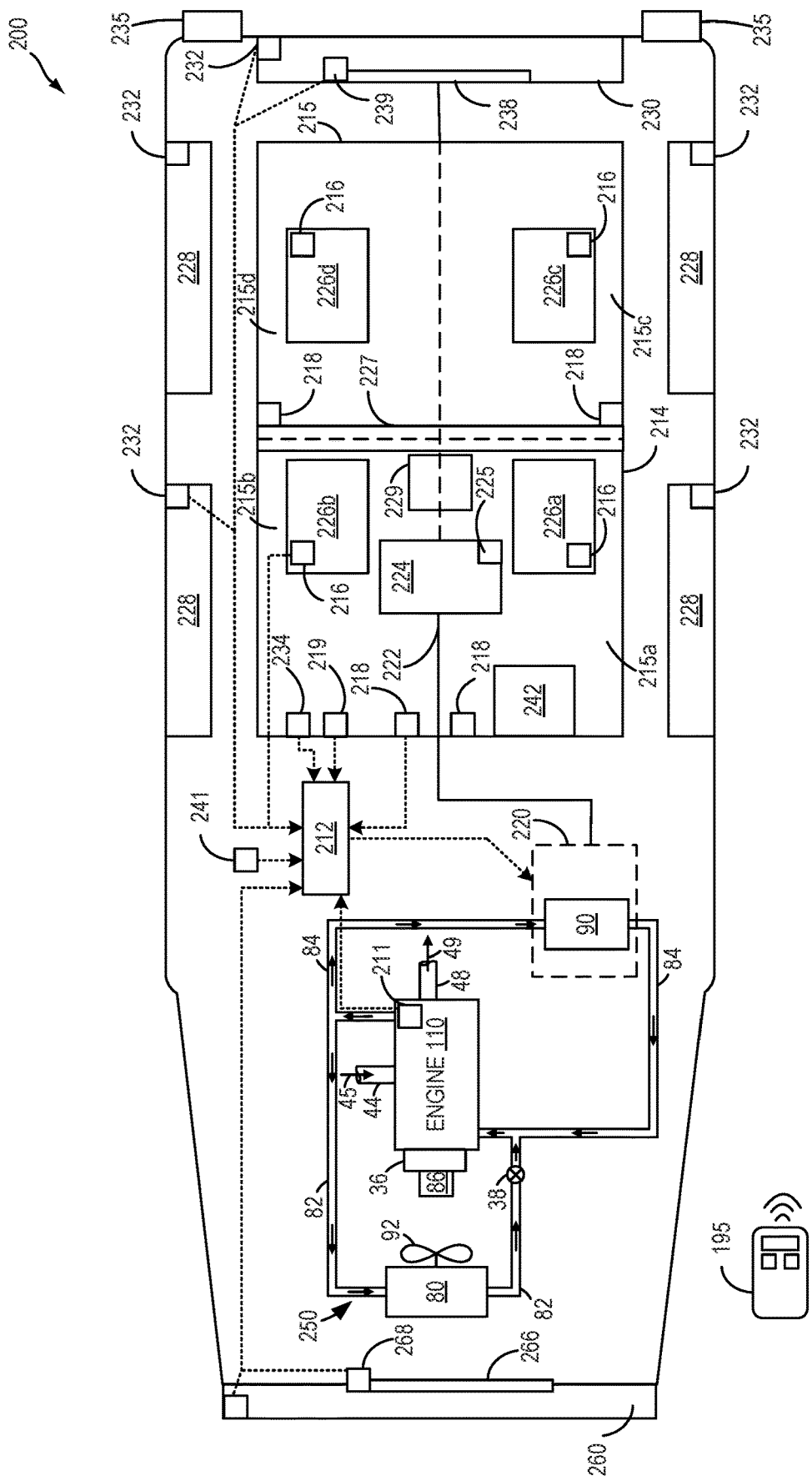
FIG. 2 schematically shows an example engine cooling system and an example HVAC system in a motor vehicle.
Figure 5:
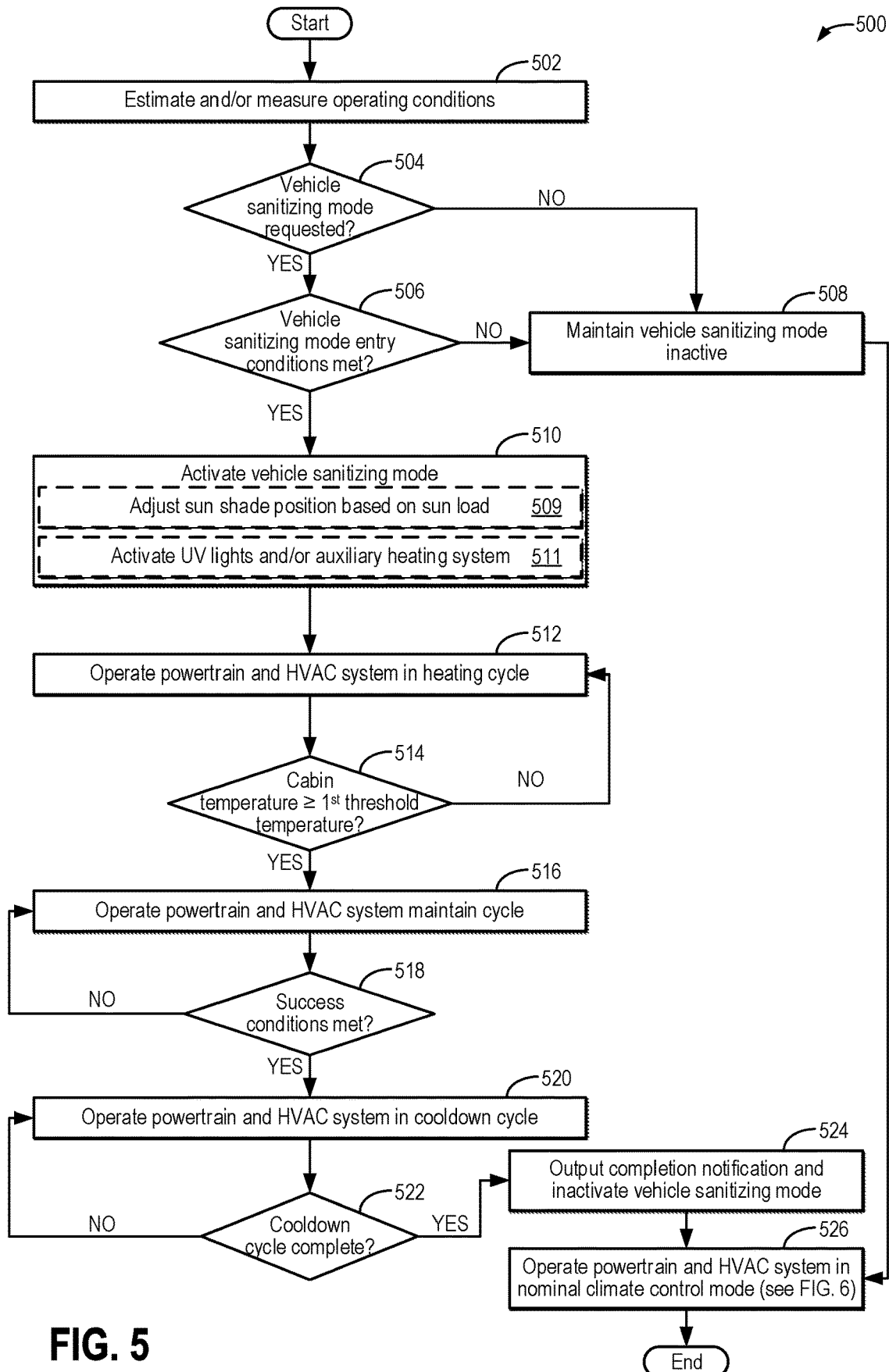
FIG. 5 shows a high-level flow chart of an example method for operating a vehicle in a vehicle sanitizing mode.
Figure 6:
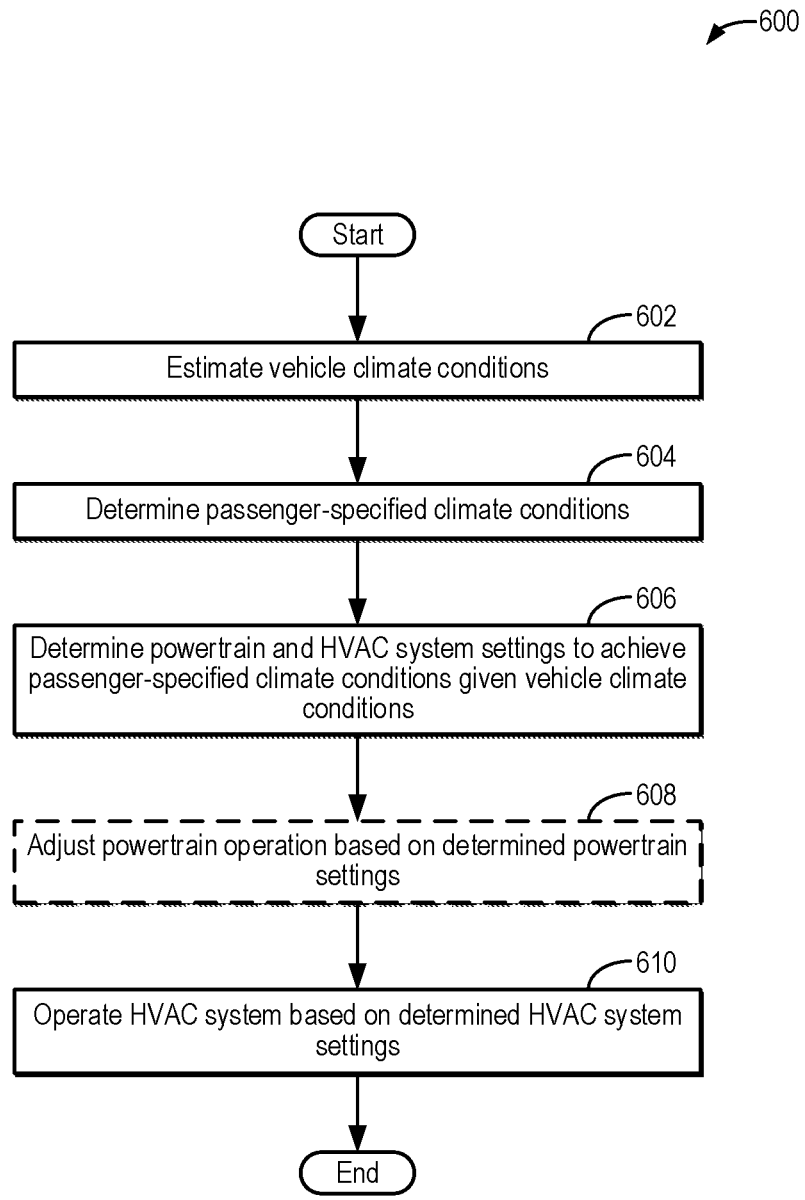
FIG. 6 shows a flow chart of an example method for operating a vehicle in a nominal climate control mode.
Figure 7:
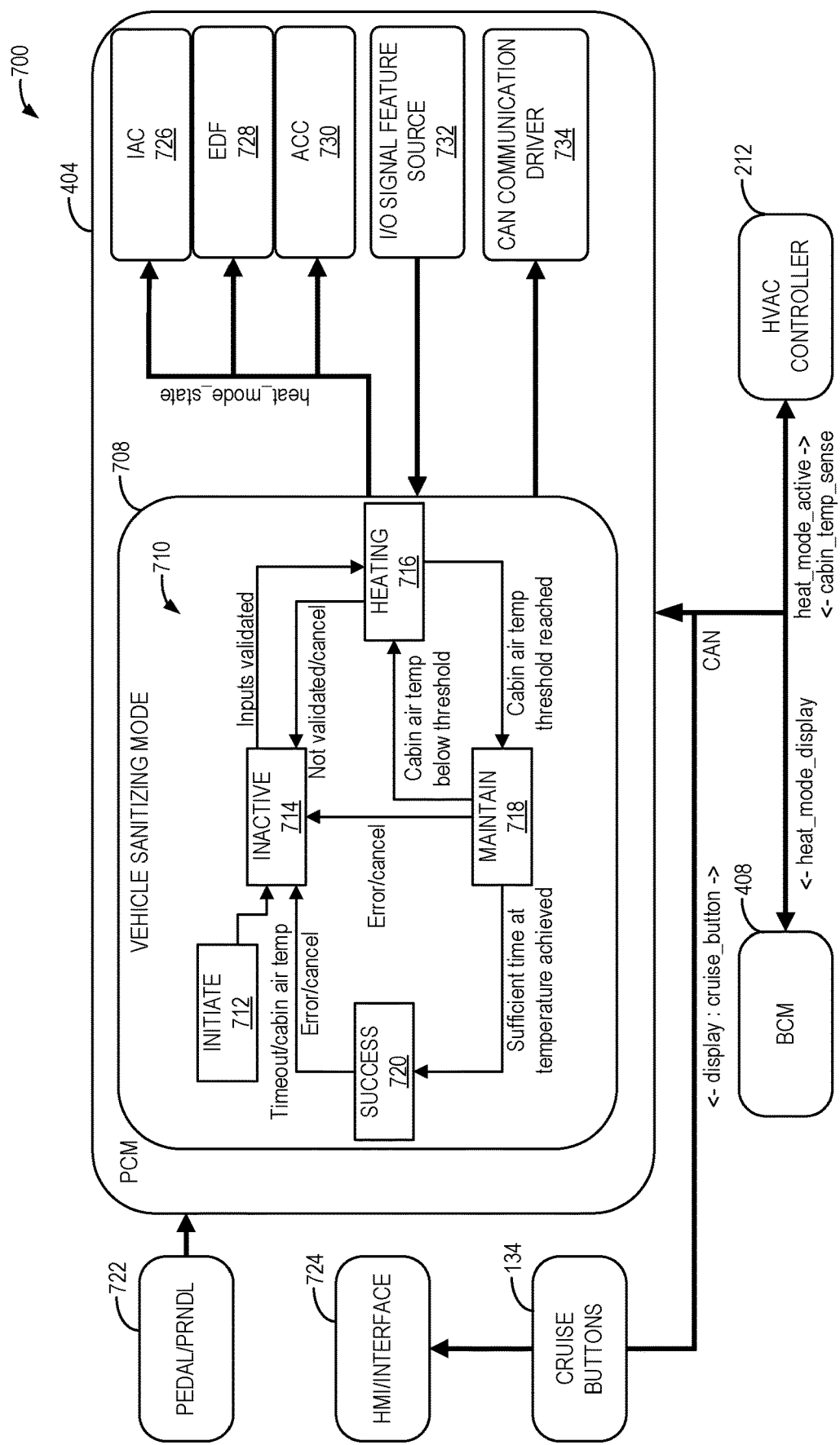
FIG. 7 shows an example system-level block diagram that may be used to execute the method of FIG. 5.

The following description relates to systems and methods for heat sanitizing a vehicle, which may be the vehicle shown in FIG. 2. The vehicle may be propelled via the vehicle propulsion system shown in FIG. 1, for example, and may include a heating, ventilation, and air-conditioning (HVAC) system for climate control and passenger comfort, such as the HVAC system shown in FIG. 3. Further, the vehicle may include a control system including a control architecture, such as the high-level control architecture of FIG. 4, for operating in a vehicle sanitizing mode. A method for operating in the vehicle sanitizing mode is shown in FIG. 5, which may enable the HVAC system to deliver higher temperature air to a cabin of the vehicle than in a nominal climate control mode, a method for which is shown in FIG. 6. In some examples, operating in the vehicle sanitizing mode may be performed while the vehicle is receiving power from an external power source as a part of or prior to vehicle preconditioning, such as according to the method of FIG. 10. FIG. 7 shows a system-level block diagram of the vehicle sanitizing mode described in FIG. 5. Further, FIGS. 8A and 8B and 9A and 9B show example timelines of powertrain and HVAC system adjustments that may be performed during the vehicle sanitizing mode in contrast to the nominal climate control mode.

FIG. 1 illustrates an example vehicle propulsion system 100. Vehicle propulsion system 100 includes a fuel burning engine 110 and a motor 120. As a non-limiting example, engine 110 comprises an internal combustion engine, and motor 120 comprises an electric motor. Motor 120 may be configured to utilize or consume a different energy source than engine 110. For example, engine 110 may consume a liquid fuel (e.g., gasoline) to produce an engine output, while motor 120 may consume electrical energy to produce a motor output. As such, a vehicle with vehicle propulsion system 100 may be referred to as a hybrid electric vehicle (HEV). However, in other examples, vehicle propulsion system 100 may be a traditional vehicle including only engine 110 (and not motor 120) or an all-electric vehicle (EV) including only motor 120 (and not engine 110). Further, in some examples, engine 110 may be coupled to an engine cooling system and a heating, ventilation, and air conditioning (HVAC) system, as will be described with respect to FIGS. 2 and 3.

Vehicle propulsion system 100 may be included in a vehicle, such as a passenger car, truck, etc., and may utilize a variety of different operational modes depending on operating conditions encountered by the vehicle. Some of these modes may enable engine 110 to be maintained in an off state (e.g., set to a deactivated state) where combustion of fuel at the engine is discontinued and the engine is at rest. For example, under select operating conditions, motor 120 may propel the vehicle via a drive wheel 130, as indicated by an arrow 122, while engine 110 is deactivated.

During other operating conditions, engine 110 may be set to a deactivated state (as described above) while motor 120 may be operated to charge an energy storage device 150. For example, motor 120 may receive wheel torque from drive wheel 130, as indicated by arrow 122, and may convert the kinetic energy of the vehicle to electrical energy for storage at energy storage device 150, as indicated by an arrow 124. This operation may be referred to as regenerative braking of the vehicle. Thus, motor 120 may function as a generator in some examples. However, in other examples, a generator 160 may instead receive wheel torque from drive wheel 130 and may convert the kinetic energy of the vehicle to electrical energy for storage at energy storage device 150, as indicated by an arrow 162. As an additional example, motor 120 may use energy stored at energy storage device 150 to crank engine 110 in a starting operation. Energy storage device may include one or more batteries. For example, energy storage device may include one or more traction batteries and/or one or more starting, lighting, and ignition (SLI) batteries.

During still other operating conditions, engine 110 may be operated by combusting fuel received from a fuel system 140, as indicated by an arrow 142. For example, engine 110 may be operated to propel the vehicle via drive wheel 130, as indicated by an arrow 112, while motor 120 is deactivated. During other operating conditions, both engine 110 and motor 120 may each be operated to propel the vehicle via drive wheel 130, as indicated by arrows 112 and 122, respectively. A configuration where both the engine and the motor may selectively propel the vehicle may be referred to as a parallel type vehicle propulsion system. Note that in some examples, motor 120 may propel the vehicle via a first set of drive wheels and engine 110 may propel the vehicle via a second set of drive wheels.

In other examples, vehicle propulsion system 100 may be configured as a series type vehicle propulsion system, whereby the engine does not directly propel the drive wheels. Rather, engine 110 may be operated to power motor 120, which may in turn propel the vehicle via drive wheel 130, as indicated by arrow 122. For example, during select operating conditions, engine 110 may drive generator 160, as indicated by an arrow 116, which may in turn supply electrical energy to one or more of motor 120, as indicated by an arrow 114, or energy storage device 150, as indicated by arrow 162. As another example, engine 110 may be operated to drive motor 120, which may in turn function as a generator to convert the engine output to electrical energy. The electrical energy may be stored at energy storage device 150 for later use by the motor, for example.

Fuel system 140 may include one or more fuel tanks 144 for storing fuel on-board the vehicle, one or more fuel pumps, and one or more fuel rails. For example, fuel tank 144 may store one or more liquid fuels, including (but not limited to) gasoline, diesel, and alcohol fuels. In some examples, the fuel may be stored on-board the vehicle as a blend of two or more different fuels. For example, fuel tank 144 may be configured to store a blend of gasoline and ethanol (such as E10, E85, etc.) or a blend of gasoline and methanol (such as M10, M85, etc.), whereby these fuels or fuel blends may be delivered to engine 110 as indicated by arrow 142. Still other suitable fuels or fuel blends may be supplied to engine 110, where they may be combusted to produce an engine output (e.g., torque). The engine output may be utilized to propel the vehicle (as indicated by arrow 112) or to recharge energy storage device 150 via motor 120 or generator 160.

In some examples, energy storage device 150 may be configured to store electrical energy that may be supplied to other electrical loads residing on-board the vehicle (other than the motor), including HVAC system components, engine starting components, headlights, cabin audio and video systems, etc. As a non-limiting example, energy storage device 150 may include one or more batteries and/or capacitors.

A control system 190 may communicate with one or more of engine 110, motor 120, fuel system 140, energy storage device 150, and generator 160. Control system 190 may receive sensory feedback information from one or more of engine 110, motor 120, fuel system 140, energy storage device 150, and generator 160. Further, control system 190 may send control signals to one or more of engine 110, motor 120, fuel system 140, energy storage device 150, and generator 160 responsive to this sensory feedback. Further still, control system 190 may include a plurality of controllers (or control modules). Each of the plurality of controllers may include a microprocessor unit, input/output ports, an electronic storage medium for executable programs (e.g., executable instructions) and calibration values, such as a non-transitory read-only memory (ROM) chip, random access memory (RAM), keep alive memory (KAM), and a data bus. The plurality of controllers may communicate with each other over a controller area network (CAN), for example, as will be further described with respect to FIG. 4.

Control system 190 may receive an indication of an operator requested output of the vehicle propulsion system 100 from a vehicle operator 102. For example, control system 190 may receive sensory feedback from a pedal position sensor 194 concerning a position of a pedal 192. Pedal 192 may refer schematically to a brake pedal and/or an accelerator pedal that may be depressed by vehicle operator 102. Furthermore, in some examples, control system 190 may receive wireless signals from a key fob 195 having a remote start button 105. In other examples (not shown), a remote engine start may be initiated via a cellular telephone or a smartphone-based system where a user's telephone sends data to a server, and the server communicates with the vehicle to start the engine.

Energy storage device 150 may periodically receive electrical energy from a power source 180 residing external to the vehicle (e.g., an external stationary power grid that is not part of the vehicle), as indicated by an arrow 184. As a non-limiting example, vehicle propulsion system 100 may be configured as a plug-in HEV, whereby electrical energy may be supplied to energy storage device 150 from power source 180 via an electrical energy transmission cable 182. During a recharging operation of energy storage device 150 from power source 180, electrical energy transmission cable 182 may electrically couple energy storage device 150 and power source 180. While the vehicle system is operated to propel the vehicle, electrical energy transmission cable 182 may be disconnected between power source 180 and energy storage device 150. Control system 190 may identify and/or control an amount of electrical energy stored at the energy storage device, which may be referred to as a state of charge (SOC).

In other examples, electrical energy transmission cable 182 may be omitted, where electrical energy may be received wirelessly at energy storage device 150 from power source 180. For example, energy storage device 150 may receive electrical energy from power source 180 via one or more of electromagnetic induction, radio waves, and electromagnetic resonance. As such, it should be appreciated that any suitable approach may be used for recharging energy storage device 150 from a power source that does not comprise part of the vehicle. In still other examples, vehicle propulsion system 100 may not receive power from a power source that does not comprise part of the vehicle. In this way, motor 120 may propel the vehicle by utilizing an energy source other than the fuel utilized by engine 110.

Fuel system 140 may periodically receive fuel from a fuel source residing external to the vehicle. As a non-limiting example, vehicle propulsion system 100 may be refueled by receiving fuel via a fuel dispensing device 170, as indicated by an arrow 172. In some examples, fuel tank 144 may be configured to store the fuel received from fuel dispensing device 170 until it is supplied to engine 110 for combustion. In some examples, control system 190 may receive an indication of the level of fuel stored in fuel tank 144 via a fuel level sensor. The level of fuel stored in fuel tank 144 (e.g., as identified by the fuel level sensor) may be communicated to the vehicle operator, for example, via a fuel gauge or indication in a human machine interface (HMI) 196. HMI 196 may include an instrument panel, a message center, etc. and may be configured to both receive inputs from the vehicle operator and output information to the vehicle operator. HMI 196 may include indicator light(s) and/or a text-based display in which messages are displayed to the operator. HMI 196 may also include various input devices for receiving inputs from the vehicle operator, such as buttons, touch screens, voice input/recognition, etc.

In some examples, control modules of control system 190 may be placed in a reduced power mode or sleep mode, wherein the control modules maintain data-retaining functions only and operate with a lower battery consumption than in a corresponding awake mode. For example, the control modules may be placed in the sleep mode following a vehicle key-off event (e.g., a human driver removing a key from a vehicle, leaving the proximity of the vehicle with a key fob, and/or otherwise instructing the vehicle to be in an off/inoperative state, at which time the engine may be stopped rotating and electrical propulsion devices, if present, may be deactivated). Control system 190 may have a wake input that allows the control modules to be returned to the awake mode based on an input received from one or more sensors. For example, the opening of a vehicle door may trigger a return to an awake mode. In other examples, the control modules may be awoken in order to execute one or more afterrun tasks, including diagnostic and non-diagnostic features, to operate in a vehicle sanitizing mode, and/or to perform vehicle preconditioning, as will be further described with respect to FIGS. 5 and 10. In such an example, a timer or alarm for waking the control modules may be set based on received user input such that the control modules may be awoken to perform the requested tasks before the vehicle is turned on by the user, as further described herein. For example, when the timer elapses, a circuit may wake the control modules to operate in the vehicle sanitizing mode and/or to perform vehicle preconditioning without additional input from the user (e.g., the vehicle operator).

Control system 190 may be communicatively coupled to other vehicles or infrastructures using appropriate communications technologies. For example, control system 190 may be coupled to other vehicles or infrastructures via a wireless network 131, which may comprise Wi-Fi, Bluetooth® wireless technology, a type of cellular service, a wireless data transfer protocol, and so on. Control system 190 may broadcast (and receive) information regarding vehicle data, vehicle diagnostics, traffic conditions, vehicle location information, vehicle operating procedures, etc., via vehicle-to-vehicle (V2V), vehicle-to-infrastructure-to-vehicle (V2I2V), and/or vehicle-to-infrastructure (V2I or V2X) technology. Information exchanged between vehicles may be directly communicated between vehicles or via multi-hop. In some examples, longer range communications (e.g. WiMax) may be used in place of or in conjunction with V2V or V2I2V to extend the coverage area. In still other examples, vehicle control system 190 may be communicatively coupled to other vehicles or infrastructures via wireless network 131 and the Internet (e.g. the Cloud).

Control system 190 may also receive input from a gear selector 108. For example, the vehicle operator may adjust a gear of a transmission by adjusting the position of gear selector 108. In the example depicted, gear selector 108 has 5 positions (park, reverse, neutral, drive, and low gear, or PRNDL). However, other numbers of positions are also possible. Further, control system 190 may receive input from cruise control buttons 134. Cruise control buttons 134 may include one or more buttons for providing input from operator 102, such as an "on" button configured to activate cruise control when depressed, an "off" button configured to deactivate cruise control when depressed, a "set+" button configured to increase a set cruise control speed when depressed, and a "set−" button configured to decrease the set cruise control speed when depressed. When cruise control is activated responsive to depression of the "on" button, control system 190 may automatically control a travel speed of the vehicle to the set cruise control speed without additional input from operator 102 via pedal 192. When cruise control is deactivated (e.g., responsive to depression of the "off" button or responsive to the "on" button not being depressed), the travel speed of the vehicle may be directly controlled by operator 102 via pedal 192.

The vehicle propulsion system 100 may also include an ambient temperature/humidity sensor 198 and a roll stability control sensor, such as a lateral and/or longitudinal and/or yaw rate sensor(s) 199, as well as an on-board navigation system 132 (for example, a Global Positioning System, GPS) that an operator of the vehicle may interact with. The navigation system 132 may include one or more location sensors for assisting in estimating vehicle speed, vehicle altitude, vehicle position/location, etc. This information may be additionally used to infer operating parameters, such as local barometric pressure. As discussed above, control system 190 may further be configured to receive information via the Internet or other communication networks. Information received from the GPS may be cross-referenced to information available via the Internet to determine local weather conditions, local vehicle regulations, etc. Thus, the control system 190 receives signals from the various sensors and other inputs of FIG. 1 and employs the various actuators of FIG. 1 to adjust vehicle system operation based on the received signals and instructions stored on a memory of the control system.

In some examples, vehicle propulsion system 100 may be included in an autonomous vehicle (AV). In such examples, operator 102 may be substituted prior to the start of or en route during a specified trip by an autonomous vehicle controller 191 included in control system 190. AV controller 191 may provide indications and/or requested output of vehicle propulsion system 100 to other control modules of control system 190. In accordance with the requests from AV controller 191, the control modules of control system 190 may actuate various vehicle actuators to propel the vehicle. In the case of an AV, vehicle propulsion system 100 may include various devices for detecting vehicle surroundings, such as radar, laser light, on-board navigation system 132, odometry, and computer vision sensors. Advanced control systems, as part of AV controller 191, may interpret sensory information to identify appropriate navigation paths as well as obstacles and relevant signage (e.g., speed limits, traffic signals, and the like). AV controller 191 may further include executable instructions that are capable of analyzing the sensory data to distinguish between different vehicles on the road, which may aid in planning a path to a desired destination, as well as executable instructions to, in combination with sensory feedback, park the vehicle in a designated or detected available parking space. For example, AV controller 191 may include executable instructions to detect a type of roadway (e.g., a one-way street, a freeway, a divided highway, and the like) or an available parking space (e.g., an empty space with enough clearance for the vehicle that is not prohibited based on time of day or loading zone, and the like). Thus, in some examples, vehicle propulsion system 100 may be controlled using input from vehicle operator 102, and in other examples, vehicle propulsion system 100 may be controlled using executable instructions included in AV controller 191 and without input from vehicle operator 102, such as when vehicle operator 102 is not present.

Further, in some examples, vehicle propulsion system 100 may be included in a car-sharing vehicle. In such an example, control system 190 may include a car-sharing module 193. Car-sharing module 193 may include software, such as executable instructions stored on non-memory, that enables the vehicle propulsion system 100 to be operated by a plurality of different operators. As one example, car-sharing module 193 may enable key-less operation of vehicle propulsion system 100. For example, car-sharing module 193 may communicate with a smartphone app to change an ignition status of vehicle propulsion system 100, a door lock status, etc. Further, car-sharing module 193 may track the usage of vehicle propulsion system 100 by each different operator. For example, car-sharing module 193 may communicate the usage information to a remote server via wireless network 131.

Next, FIG. 2 shows a schematic depiction of a vehicle 200 equipped with an engine cooling system 250 and an HVAC system 220. The vehicle 200 may be propelled by vehicle propulsion system 100 shown in FIG. 1. As such, components previously introduced in FIG. 1 are numbered the same and may not be reintroduced. Further, although not explicitly shown, vehicle 200 may include all or some of the components shown in FIG. 1.

Vehicle 200 includes a cabin space 214. Cabin space 214 may be divided into occupancy zones 215. In the example shown, vehicle 200 is a four-passenger vehicle, although other examples may include different occupancy numbers. Accordingly, cabin space 214 may be divided into four occupancy zones including a left front side driver zone 215a having a left front seat 226a, a right front side passenger zone 215b having a right front seat 226b, a rear left side passenger zone 215c having a left rear seat 226c, and a rear right side passenger zone 215d having a right rear seat 226d. Each occupancy zone may be equipped with an occupancy sensor 216, which may be configured to identify whether or not a passenger is present in the seat in the corresponding occupancy zone. For example, each occupancy sensor 216 may be a seat weight sensor. As another example, each occupancy sensor 216 may additionally or alternatively include one or more of an interior camera, an infrared camera, an interior microphone, and a carbon dioxide sensor. Further, in the example shown, a partition 227 is positioned between the front seats (e.g., the left front seat 226a and the right front seat 226b) and the rear seats (e.g., the left rear seat 226c and the right rear seat 226d). Partition 227 may provide a physical barrier between the front seats and the rear seats, for example. Partition 227 may be comprised of metal (such as one or more of aluminum and steel) and/or a transparent polymer (e.g., polycarbonate) and may include openings or slits. In some examples, partition 227 may include expanded metal or perforated metal sheets coupled to metal cage.

HVAC system 220 may be configured to provide a climate-controlled air flow to cabin space 214 through ducting 222 and one or a plurality of vents 224. While the depicted example shows one vent for the entire cabin space, it will be appreciated that each occupancy zone may be serviced by distinct vents to enable each passenger to control the climate (for example, the temperature) of their occupancy zone. HVAC system 220 may additionally provide a climate-controlled air flow to the vehicle floor and panels through appropriate ducting, as will be elaborated below with respect to FIG. 3. Vent 224 may also comprise vent sensor 225, which can provide an HVAC controller 212, for example, an input indication of a blower motor speed, a direction of air flow from the vent, and a duration of time and degree that the vent is open.

In some examples, vehicle 200 further includes an auxiliary heating system 290. Auxiliary heating system 290 may include a heat exchanger that can generate heat while engine 110 is off. In the example shown, auxiliary heating system 290 includes a parking heater 292 that combusts fuel received from a fuel tank 294 to heat air or coolant received at an inlet 296 and supplied to HVAC system 220 at an outlet 298. Via HVAC system 220, the coolant or air may be used to heat both cabin space 214 and engine 110 (e.g., by heating coolant supplied to engine 110). The fuel stored in fuel tank 294 may be a same or different type of fuel as supplied to engine 110. For example, the fuel stored in fuel tank 294 may be diesel, gasoline, propane, or another combustible fuel.

Auxiliary heating system 290 may be activated via user input to a remote device, at least in some examples. The remote device may be a remote control or smartphone, for example, such as a smartphone 295 shown in FIG. 2. Additionally or alternatively, auxiliary heating system 290 may be activated manually, such as by the user flipping a switch or depressing a power button of auxiliary heating system 290, or may be activated according to a pre-set timer. In still other examples, additionally or alternatively, auxiliary heating system 290 may be activated by control system 190 shown in FIG. 1. For example, the control system may activate auxiliary heating system 290 responsive to an anticipation of a vehicle start, such as according to learned/predicted driving routes (e.g., routes that are frequented according to a daily, weekly, or monthly schedule within a common time of day and day of the week). In another example, the control system may activate auxiliary heating system 290 responsive to a request for operating in a vehicle sanitizing mode, as will be elaborated below with respect to FIG. 5.

Activating auxiliary heating system 290 may include supplying fuel and air to parking heater 292. For example, fuel may be supplied to auxiliary heating system 290 from fuel tank 294 via a fuel metering pump and air may be inducted via a rotating motor fan. The fuel metering pump and the rotating motor fan may be electrically controlled, and thus, activating auxiliary heating system 290 may also include supplying electrical power to auxiliary heating system 290, such as from energy storage device 150 shown in FIG. 1 or a dedicated power source of auxiliary heating system 290. The air and fuel may be ignited within a combustion chamber of parking heater 292, thereby producing hot combustion gases. Heat may be transferred from the hot combustion gases to air or coolant via a heat exchanger of parking heater 292, and the heated air or coolant may then flow to HVAC system 220 and/or engine 110. In this way, auxiliary heating system 290 may heat cabin space 214 and engine 110 while engine 110 is off.

Cabin space 214 may be equipped with a temperature sensor 218 and a humidity sensor 219 to provide feedback to HVAC controller 212 regarding the temperature and humidity conditions, respectively, in the cabin space. In one example, temperature sensor 218 may be a single temperature sensor providing feedback regarding an average temperature of the cabin space. In another example, multiple temperature sensors 218 may be included, such as one temperature sensor 218 per occupancy zone, to provide feedback to HVAC controller 212 regarding the temperature conditions within each occupancy zone. Alternatively, the signal provided from the multiple temperature sensors 218 may be combined and arranged in HVAC controller 212 to provide a control input signal representative of the temperature of the cabin space 214. Similarly, cabin space 214 may include one or a plurality of humidity sensors 219 for providing feedback regarding an average humidity of the cabin space to HVAC controller 212.

The vehicle 200 may be configured with four side doors 228, each including a side window. In other examples, the vehicle may be configured with two side doors or another number of side doors. Additionally, the vehicle 200 may include a rear window 230 that may be part of a rear vehicle door. Rear window 230 may also comprise a hatch, or larger portals such as a bus door, no door (for example, as in some delivery vehicles), portals with no window panes, and the like. Each vehicle side door 228 and rear window 230 may include a sensor 232 configured to provide an indication to HVAC controller 212 of the closed or open position of the door and/or window. Sensors 232 may represent one or a plurality of sensors at each door/window.

In addition to rear window 230, vehicle 200 may further include a rear window vent 238 and rear window vent sensor 239. Sensors 232, rear window vent 238, and rear window vent sensor 239 may provide inputs to HVAC controller 212. Rear windshield vent sensor 239 may provide HVAC controller 212 with an input indication, for example, of a blower speed and a duration of time and degree that rear window vent 238 is open. Vehicle 200 may further include a front window or windshield 260, a front windshield vent 266, and a front windshield vent sensor 268. Front windshield vent sensor 268 may provide an input to the HVAC controller 212 regarding, for example, a fan speed and a duration of time and degree that the vent is open.

Cabin space 214 may also be equipped with one or more sun load sensors 234 (only one of which is shown in FIG. 2) to provide a signal indicative of the solar load received from each window of a respective occupancy zone 215 to HVAC controller 212. The signal provided from the sun load sensors 234 may be combined and arranged in HVAC controller 212 to provide a control input signal representative of the solar radiation intensity on the vehicle interior. Alternatively, the signals from the distinct sun load sensors may be used individually as a control input signal representative of the solar radiation intensity of each occupancy zone 215. The signal received from the sun load sensors 234 may be used for climate control, as will be described with respect to FIG. 6, and may also be used for automatically activating exterior lights 235 and/or interior lights 229.

Vehicle 200 additionally may be equipped with and a roof window 255, which may be a sun roof or moon roof, for example. Roof window 255 may enable ambient light to enter cabin space 214 from a top of the vehicle based on a position of a sun shade 256. For example, roof window 255 may be comprised of a transparent panel (e.g., glass) that enables light transmission, and sun shade 256 may be an opaque panel that blocks light transmission. The position of sun shade 256 may be adjusted with respect to roof window 255 to adjust an amount of light transmitted through roof window 255 into cabin space 214. For example, roof window 255 may be fixed in place, and sun shade 256 may translate (e.g., slide) with respect to roof window 255. Sun shade 256 may be adjusted between a plurality of positions via a sun shade actuator 258. For example, the plurality of positions may range from a fully closed position, where sun shade 256 maximally (e.g., fully) blocks light transmission through roof window 255 to a fully open position, where sun shade 256 minimally blocks light transmission through roof window 255 (e.g., light transmission through roof window 255 is maximal). In some examples, sun shade actuator 258 is a manually operated actuator, such as a hand crank or handle. In other examples, sun shade actuator 258 is an electronic actuator that receives an electronic control signal from a controller, such as HVAC controller 212 or another controller of the vehicle 200. Additionally, vehicle 200 may include fore and aft sun load sensors 234 on roof window 255, which may provide a control input signal to HVAC controller 212 representative of the solar radiation intensity on the roof window 255. As another example, sun shade 256 may provide thermal insulation to cabin space 214. For example, heat transmission between the environment and cabin space 214 via roof window 255 may increase as a degree of opening of sun shade 256 increases and may decrease as the degree of opening of sun shade 256 decreases. Thus, when the temperature of cabin space 214 is lower than the ambient temperature, (fully) closing sun shade 256 may decrease heat transfer from the environment to cabin space 214, and when the temperature of cabin space 214 is higher than the ambient temperature, (fully) closing sun shade 256 may decrease heat transfer from cabin space 214 to the environment. Similarly, when the temperature of cabin space 214 is lower than the ambient temperature, (fully) opening sun shade 256 may increase heat transfer from the environment to cabin space 214, and when the temperature of cabin space 214 is higher than the ambient temperature, (fully) opening sun shade 256 may increase heat transfer from cabin space 214 to the environment.

Additional sensors, such as an altitude sensor and an air quality sensor, may also be included in cabin space 214 (or each occupancy zone 215) and may provide inputs to the HVAC controller 212. Ambient temperature/humidity sensor 198 of FIG. 1 may also provide input to the HVAC controller 212. HVAC controller 212 may also receive an indication of the ignition state of engine 110 from an ignition sensor. Vehicle 200 may further include a key fob sensor 241 configured to receive input from key fob 195. Specifically, key fob sensor 241 may remotely couple the vehicle 200 to key fob 195, thereby enabling a remote, key-less entry into vehicle 200. Key fob sensor 241 may be configured to provide an indication to HVAC controller 212 regarding the locked or unlocked position of the vehicle doors, for example. Additionally, vehicle 200 may include exterior lights 235, shown schematically as tail lights in FIG. 2, and one or more interior lights 229. Exterior lights 235 may further include headlights, for example, and the one or more interior lights 229 may include instrument panel lights, dome lights, courtesy lights, etc.

In some examples, vehicle 200 may further include an ultraviolet germicidal irradiation (UVGI) system 280. UVGI system 280 may include a plurality of UV light sources 281, which may be light-emitting diodes (LEDs) or mercury-vapor lamps, for example, that emit light in the ultraviolet (UV) wavelength range. In particular, the light emitted by the plurality of UV light sources 281 of UVGI system 280 may be short-wavelength UVC light (e.g., having a wavelength between 100 and 280 nanometers). The plurality of UV light sources 281 may be distributed throughout cabin space 214 to direct UV light toward a plurality of interior vehicle surfaces. The UV light may kill or inactivate microorganisms, such as bacteria, viruses, and molds, on the irradiated surfaces. In some examples, control system 190 shown in FIG. 1 may activate UVGI system 280, causing the plurality of UV light sources 281 to emit UV light, responsive to a request to operate in a vehicle sanitizing mode, as will be elaborated with respect to FIG. 5, or according to another pre-programmed disinfection schedule. In some examples, the UVGI system 280 may only be activated responsive to an indication that the vehicle is unoccupied, as determined from the output of the occupancy sensors 216.

HVAC system 220 includes a plurality of heating and cooling components that will be described with respect to FIG. 3, such as an evaporator and a blower. HVAC system 220 also includes a heater core 90, which is shared by engine cooling system 250. As shown in FIG. 2, engine 110 may receive intake air 45 via an intake passage 44 and may exhaust combustion gases 49 via an exhaust passage 48. Engine cooling system 250 circulates coolant through engine 110 to absorb waste engine heat and distribute the heated coolant to a radiator 80 and/or heater core 90 via coolant lines 82 and 84, respectively.

As shown, engine cooling system 250 is coupled to engine 110 and circulates engine coolant from engine 110 to radiator 80 and back to engine 110 via a water pump 86 and coolant line 82. Specifically, water pump 86 circulates coolant through passages in the engine block, head, etc., to absorb engine heat, which is then transferred via the radiator 80 to ambient air. Water pump 86 may be coupled to the engine a via front end accessory drive (FEAD) 36 and rotated in proportion with engine speed via a coupler, chain, etc. However, in other examples, water pump 86 may be driven by an electric motor and not by the engine. In such an example, the speed of water pump 86 may not be proportional to the speed of engine 110. In one example, where water pump 86 is a centrifugal pump, the pressure (and resulting flow) produced may be proportional to the crankshaft speed, which in the example of FIG. 2, is directly proportional to engine speed. The temperature of the coolant may be regulated by a thermostat valve 38, located in coolant line 82, which may be kept closed until the coolant reaches a threshold temperature. Further, an engine coolant temperature (ECT) sensor 211 may provide feedback to HVAC controller 212 regarding a temperature of the engine coolant, and thus of engine 110.

Further still, an engine cooling fan 92 may be coupled to radiator 80 in order to maintain an air flow through radiator 80 when vehicle 200 is moving slowly or stopped while the engine is running. In some examples, a speed of engine cooling fan 92 may be controlled by control system 190 of FIG. 1. Alternatively, engine cooling fan 92 may be coupled to water pump 86.

Hot coolant may flow through coolant line 82, as described above, and/or through coolant line 84 to heater core 90, where the heat may be transferred to cabin space 214 via HVAC system 220 before the coolant flows back to engine 110. Heater core 90 may thus act as a heat exchanger between the coolant and cabin space 214. Fins may be attached to the heater core to increase the surface area for heat transfer. Air may be forced past the fins, for example by operating a fan, to expedite heating of cabin space 214.

However, in other examples, HVAC system 220 may additionally or alternative include an electric heater. For example, heater core 90 may alternatively be an electric heater including a ceramic heater core or electric heating elements that convert electric current (e.g., supplied from energy storage device 150 of FIG. 1) into heat. As another example, HVAC system may include an auxiliary electric heater in addition to heater core 90. As one example, the electric heater, whether auxiliary or comprising heater core 90, may be an air-side or liquid (e.g., coolant-side) positive temperature coefficient (PTC) heater that is operated to increase a temperature of air provided to cabin space 214.

In some examples, water pump 86 may operate to circulate the coolant through both coolant lines 82 and 84. In other examples, an electric auxiliary pump (not shown) may be included upstream of heater core 90 in the HVAC system 220 in addition to the engine-driven pump. Therein, the auxiliary pump may be employed to circulate coolant through heater core 90 during occasions when engine 110 is off (e.g., electric only operation) and/or to assist the engine-driven water pump 86 when the engine is running. Like water pump 86, the auxiliary pump may be a centrifugal pump; however, the pressure (and resulting flow) produced by the auxiliary pump may be proportional to an amount of power supplied to the pump by a system energy storage device (e.g., energy storage device 150 of FIG. 1).

As noted herein, the amount of waste heat generated by the engine and transferred to the coolant may affect the amount of heat that may be transferred to the passenger compartment to provide cabin heating. For example, during engine idling conditions, the amount of waste heat generated may be proportionally reduced, thereby reducing an amount of cabin heating available. Further, during such conditions, cabin heating may be substantially slow. As elaborated herein with reference to FIGS. 4-7, HVAC controller 212 may communicate with an engine controller, such as a powertrain control module (PCM), to adjust the engine idle speed in order to increase or decrease the amount of waste heat provided. Specifically, the engine idle speed may be selectively increased (e.g., from a default engine speed) to increase the amount of waste heat that is generated at engine idle and circulated through the HVAC system 220 via coolant. In this way, by generating waste heat during vehicle idling, HVAC system heating may be expedited and increased to a higher temperature, thereby enabling heat-based vehicle sanitization.

Continuing with FIG. 2, the vehicle 200 may include a climate-control interface 242, where environmental settings or set-points for a level of thermal comfort desired in the cabin space may be selected. Therein, an amount of heating or cooling of the cabin space 214 may be requested. For example, a temperature set-point of the cabin may be selected. Additionally, a direction of air flow may be specified. For example, the air flow may be directed towards the floor of the vehicle, towards the passenger seats, other areas in the interior of the vehicle, and the like. The user may also specify a rate of air flow (for example, low, medium or high flow rates). Further, the settings may specify a ratio of fresh air (from outside the vehicle) to recirculated air (from inside the vehicle). Further still, the settings may specify the directing of the air flow toward vehicle panels for defrosting and/or defogging operations. In some examples, each occupancy zone 215 may include respective climate-control interfaces to enable each occupancy zone to be configured with respective climate-controlled zones.

In some examples, vehicle 200 may further include one or more heated surfaces 270, one of which is illustrated in FIG. 2. The one or more heated surfaces 270 may include electronically controlled heating elements, radiant panels, and/or fibers. As one example, the one or more heated surfaces 270 may be included in heated seats, a heated steering wheel, and heated front window and rear window components. Additionally or alternatively, the one or more heated surfaces 270 may be strategically positioned to heat areas of the cabin that are not able to directly receive climate-controlled air flow from HVAC system 220. By positioning the one or more heated surfaces 270 in areas that do not receive as much climate-controlled air flow, vehicle cabin space 214 may be more uniformly heated and may be heated more quickly than systems without the one or more heated surfaces 270.

HVAC controller 212 may be a microprocessor-based controller including a central processing unit (CPU) and associated memory, such as read only memory (ROM), random access memory (RAM), and keep alive memory (KAM), as well as input and output ports for receiving information from, and communicating information to, the various sensors, vents, climate-control interfaces, and other control modules, as will be elaborated herein.

HVAC controller 212 may operate HVAC system 220 in response to passenger-selected settings, such as a temperature and direction of air flow. Specifically, in response to the passenger-selected settings, the controller may monitor and process the various inputs received from cabin temperature sensors 218, sensors 232, etc., to adjust the function of heating and cooling components (see FIG. 3), such as the evaporator, the blower, and heater core 90, to maintain the desired temperature and direction of air flow.

Further, as further described below, HVAC controller 212 may determine a vehicle condition at least partially based on the indication of one or a plurality of vehicle portal states provided by the sensors 232. Accordingly, HVAC controller 212 may determine whether to operate HVAC system 220, maintain the operation of HVAC system 220, or discontinue operation of HVAC system 220 based in part from the signal provided by sensors 232. Further, HVAC controller 212 may determine an operating mode of HVAC system 220 based in part on information received from sensors 232, occupancy sensor 216, cabin temperature sensor 218, cabin humidity sensor 219, key fob sensor 241, and ECT sensor 211, as will be elaborated below with respect to FIG. 5.

HVAC controller 212 may further operate the HVAC system responsive to the thermal comfort of the users of vehicle 200 as indicated by the sensors 232, rear window sensors, front windshield sensors, front windshield vent sensor 268, and rear window vent sensor 239. For example, if the sensors 232 in the occupied occupancy zones 215 of the cabin, as indicated by the occupancy sensors 216, indicate that the windows have been opened for several minutes, the thermal comfort of the vehicle occupants is presumed to be adequate. Accordingly, the HVAC controller can reduce the HVAC system performance, or even turn off the HVAC system heating or cooling, to conserve fuel, and thus no longer maintain the user-requested settings. For example, a higher temperature than requested may be maintained. Furthermore, HVAC controller 212 may also communicate directly with control system 190 shown in FIG. 1, providing inputs, for example from the sensors 232, vent sensor 225, occupancy sensors 216, and other sensors associated with the HVAC system 220. Control system 190 can additionally adjust the vehicle operation, such as by adjusting engine speed or torque, in response to HVAC controller inputs, as will be elaborated below with respect to FIGS. 4-7.

Figure 3:
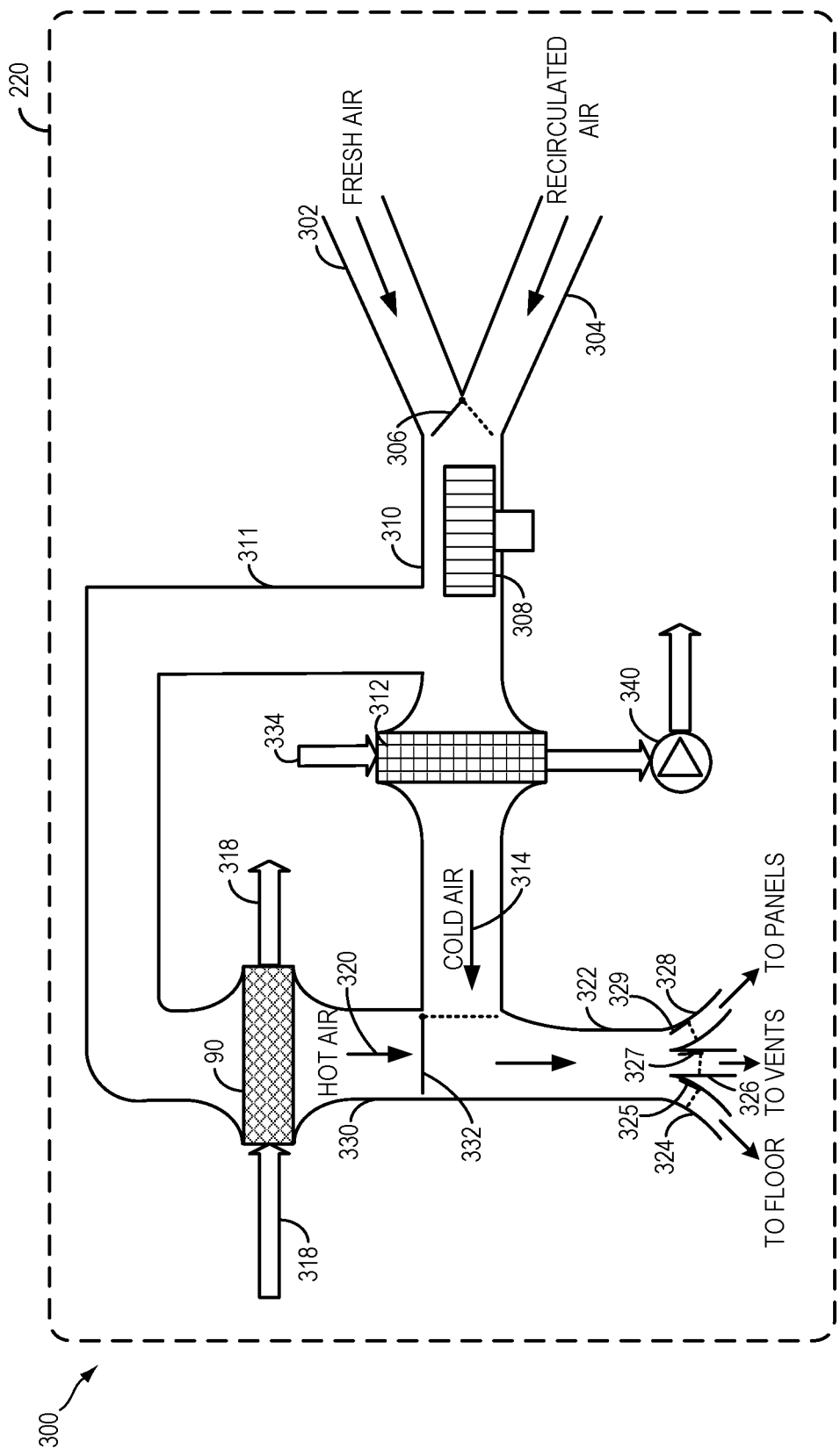
FIG. 3 illustrates an example of the HVAC system of FIG. 2.

Continuing to FIG. 3, an example embodiment 300 of the components and operation of HVAC system 220 introduced in FIG. 2 is described. Thus, components of FIG. 3 previously introduced in FIG. 2 are numbered the same. HVAC system 220 includes a fresh air duct 302 for providing fresh air from outside the vehicle and a recirculated air duct 304 for providing recirculated air from inside the vehicle cabin (e.g., cabin space 214 of FIG. 2). A ratio of fresh air to recirculated air is adjusted by adjusting a position of an air inlet door 306 responsive to selected HVAC settings. For example, when a higher proportion of recirculated air is requested, air inlet door 306 may be positioned near the mouth of fresh air duct 302 (as shown in a solid line), referred to herein as a recirculated air position. Alternatively, when a higher proportion of fresh air is requested, air inlet door 306 may be positioned near the mouth of recirculated air duct 304 (as shown in a dotted line), referred to herein as a fresh air position. Air inlet door 306 may be driven between the various positions by a vacuum motor (not shown) or may be driven by an electric servo motor (also not shown).

The requested mixture of fresh and recirculated air is passed through HVAC cooling elements configured to enable air-conditioning. Specifically, the air is passed through a blower 308 and an evaporator core 312 along a conduit 310. Blower 308 includes a variable speed blower motor and a blower wheel or fan, a speed of which may be selected increase or decrease air flow through HVAC system 220. Inside evaporator core 312, the evaporation of a low pressure cooling fluid or refrigerant 334 (for example, Freon™ refrigerant) into a low pressure gas causes a cooling effect that in turn cools the air flowing across it. Based on the temperature settings of the HVAC system, a suitable proportion of cold air 314, cooled by passage through evaporator core 312, may then be passed into ducting 322 and distributed to the cabin space, as will be elaborated below. After exiting the evaporator core, the refrigerant vapor passes through a compressor 340, emerging as a hot compressed gas. The hot compressed gas is subsequently passed through a condenser (not shown), becoming a cooled compressed liquid, after which it is fed through an expansion valve (not shown), becoming a cold liquid/vapor mixture, before finally being reintroduced into the evaporator core 312.

Similarly, hot air 320 may be generated by passage of fresh and/or recirculated air through HVAC heating components that are configured to enable air heating. Specifically, air flow generated by blower 308 is received by heater core 90 via a conduit 311. In the example shown, coolant 318, received from engine 110 of FIGS. 1-2, for example, is circulated through heater core 90. Heater core 90 may then behave as a heat exchanger, withdrawing heat from coolant 318 and transferring the withdrawn heat to air passing across it. However, in other examples, such as in electric vehicle embodiments, heater core 90 may be an electric heater, such as a PTC heater, that converts electric current (e.g., supplied from energy storage device 150 of FIG. 1) into heat, as described above with respect to FIG. 2. Thus, heater core 90 (and/or the PTC heater) are heating components that are configured to transfer heat to the air.

In this way, hot air may be generated in a conduit 330 and passed into a ducting 322. A climate-controlled air flow comprising a suitable amount of hot air and cold air may be generated in ducting 322 for subsequent passage to the cabin space. Specifically, a ratio of hot air 320 to cold air 314 may be adjusted by adjusting a position of a blend door 332 responsive to selected HVAC settings. For example, when air flow of a higher temperature is requested, blend door 332 may be positioned near the mouth of cold air conduit 310 (as shown in a dotted line), referred to herein as a hot position (or hot setting). When blend door 332 is at the hot position, maximum hot air flow from heater core 90 to ducting 322 is enabled, and cold air flow from evaporator core 312 to ducting 322 is minimized or blocked. Thus, the hot position maximizes the ratio of hot air to cold air (e.g., full hot). Alternatively, when air flow of a lower temperature is requested, blend door may be positioned near the mouth of hot air conduit 330 (as shown in a solid line), referred to herein as a cold position (or cold setting). When blend door 332 is at the cold position, maximum cold air flow from evaporator core 312 to ducting 322 is enabled, and hot air flow from heater core 90 to ducting 322 is minimized or blocked. Thus, the cold position minimizes the ratio of hot air to cold air (e.g., full cold). Blend door 332 may be driven by a vacuum motor or an electric servo motor (not shown). As such, the temperature and flow of air supplied to the cabin space may be adjusted by adjusting a ratio of hot air (generated using heating elements) and cold air (generated using cooling elements) via the position of blend door 332.

The air flow with the requested settings of flow rate and temperature may then be directed along delivery ducting 324, 326 and/or 328, which fluidically couples ducting 322 to the vehicle floor, vents, and panels, respectively, responsive to a set or requested air flow delivery location setting. In the example shown, delivery ducting 324 includes a first delivery door 325, delivery ducting 326 includes a second delivery door 327, and delivery ducting 328 includes a third delivery door 329. Each delivery door may be configured to open or close the corresponding delivery ducting, thus enabling or blocking air flow to the corresponding delivery location. For example, first delivery door 325 may be actuated between an open (e.g., fully open) position, shown in a solid line, that enables air flow through delivery ducting 324 and to the vehicle floor and a closed (e.g., fully closed) position, shown in a dashed line, that blocks air flow through delivery ducting 324. Thus, air flow is not delivered to the vehicle floor when first delivery door 325 is in the closed position. Similarly, second delivery door 327 may be actuated between an open (e.g., fully open) position, shown in a solid line, that enables air flow through delivery ducting 326 and to the vents and a closed (e.g., fully closed) position, shown in a dashed line, that blocks air flow through delivery ducting 326 and prevents air flow delivery to the vents. Further, third delivery door 329 may be actuated between an open (e.g., fully open) position, shown in a solid line, that enables air flow through delivery ducting 328 and to the panels and a closed (e.g., fully closed) position, shown in a dashed line, that blocks air flow through delivery ducting 328 and prevents air flow delivery to the panels. Each delivery door may be driven by a vacuum motor or an electric servo motor (not shown), for example. Further, in alternative examples, instead of each delivery ducting including a delivery door, a different number of delivery doors (or other flow control devices) may be used. For example, one delivery door may be included to select between the various delivery locations or combinations of delivery locations.

In this way, the heating and cooling elements of HVAC system 220 may be used to deliver an air flow with an appropriate ratio of hot and cold air with a requested flow rate to a requested location, thereby providing the vehicle passengers with a climate-controlled air flow or providing vehicle surface sanitization.

Figure 4:
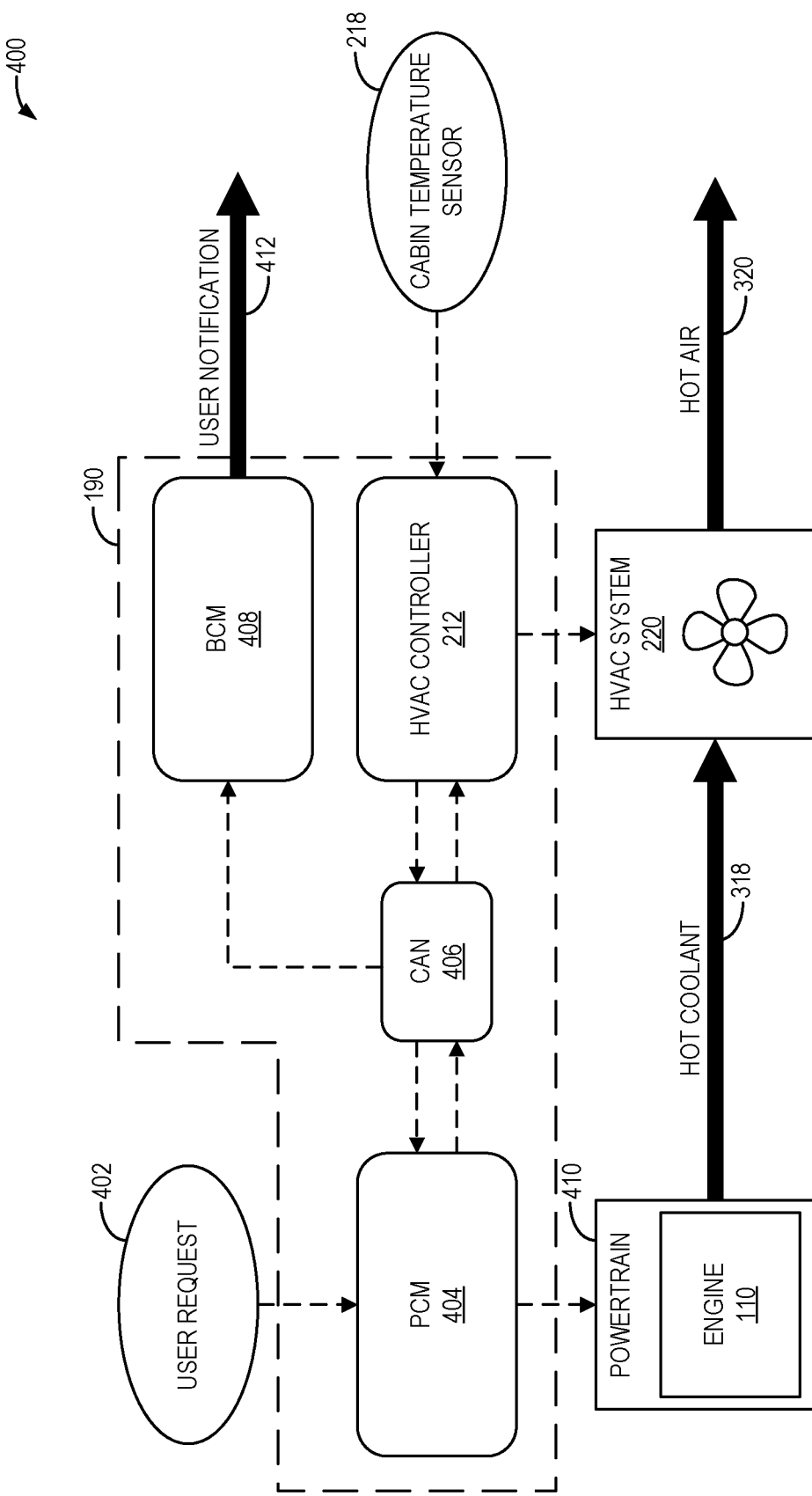
FIG. 4 schematically shows a high-level control architecture for a vehicle sanitizing mode.

Turning now to FIG. 4, a high-level control architecture 400 for a vehicle sanitizing mode is shown. Components of FIG. 4 that function the same as components described in FIGS. 1-3 are numbered the same and not re-introduced. For example, control architecture 400 shows control system 190 as including a powertrain control module (PCM) 404, a body control module (BCM) 408, and HVAC controller 212 communicating over a controller area network (CAN) 406. CAN 406 may be a gateway module, for example. PCM 404, BCM 408, and HVAC controller 212 each may be configured as a conventional microcomputer including a microprocessor unit, input/output ports, read-only memory storing executable instructions/programs and calibration values, random access memory, keep alive memory, a CAN bus, etc. As an example, PCM 404 may monitor and control a powertrain 410, including engine 110 (e.g., when the vehicle is not an electric-only vehicle), whereas BCM 408 may monitor and control various electronic accessories in the body of the vehicle, such as exterior lights 235 and interior lights 229 shown in FIG. 2. As elaborated above with respect to FIG. 2, HVAC controller 212 may monitor and control components of HVAC system 220.

As shown in FIG. 4, a user request 402 is received by PCM 404. As one example, user request 402 may be input via cruise control buttons 134 of FIG. 1. User request 402 comprises a request from a vehicle operator to operate in the vehicle sanitizing mode. As will be elaborated with regard to FIG. 5, operating in the vehicle sanitizing mode includes increasing a temperature of air output by the HVAC system 220 and provided to a vehicle cabin (e.g., cabin space 214 of FIG. 2) above that used for passenger comfort in a nominal climate control mode. Thus, PCM 404 coordinates with HVAC controller 212 over CAN 406 to raise a cabin temperature. As shown, PCM 404 and HVAC controller 212 both communicate bidirectionally with CAN 406, transmitting (e.g., sending) electronic communication signals to CAN 406 and receiving electronic communication signals from CAN 406. As one example, PCM 404 increases an idle speed of engine 110 and switches off a cooling fan (e.g., engine cooling fan 92 of FIG. 2) in order to increase a temperature of hot coolant 318 provided to HVAC system 220 (e.g., to heater core 90 of FIGS. 2 and 3), thus increasing an amount of heat available to be transferred to hot air 320. Further, HVAC controller 212 adjusts operation of various components of HVAC system 220, such as blower 308, air inlet door 306, and blend door 332 shown in FIG. 3 in order to increase the temperature of the air provided to the vehicle cabin.

Further still, HVAC controller 212 receives feedback from cabin temperature sensor 218 regarding the cabin temperature. HVAC controller 212 may further adjust components of HVAC system 220, and PCM 404 may further adjust operation of powertrain 410, responsive to the measured cabin temperature. As elaborated herein, the vehicle sanitizing mode may include a sanitization routine that is divided into a heating cycle (or phase), a maintain cycle (or phase), and a cooldown cycle (or phase). Entry into or out of each cycle may be initiated based in part on feedback received from cabin temperature sensor 218, and components of HVAC system 220 and powertrain 410 may be adjusted according to the settings for each distinct cycle.

Upon completion of the vehicle sanitizing mode, as indicated by one or more of HVAC controller 212 and PCM 404, CAN 406 outputs an electronic communication signal to BCM 408. In response, BCM 408 outputs a user notification 412. For example, the user notification 412 may include a pattern of blinking lights. In this way, the vehicle operator may be notified that the vehicle sanitizing mode is complete as well as a completion status (e.g., successful or unsuccessful), as will be elaborated below with respect to FIGS. 5 and 7.

Next, FIG. 5 shows a method 500 for heat-cleaning an interior of a vehicle by operating in a vehicle sanitizing mode. The vehicle may be vehicle 200 shown in FIG. 2 and may be propelled by vehicle propulsion system 100 of FIG. 1, for example. Further, the vehicle may include an HVAC system, such as HVAC system 220 shown in FIGS. 2 and 3, which may be advantageously used to provide heat sanitization. Instructions for carrying out method 500 and the rest of the methods included herein may be executed by one or more control modules or controllers of a control system (e.g., control system 190 of FIGS. 1 and 4) based on instructions stored on one or more memories of the control system and in conjunction with signals received from sensors of the vehicle system, such as the sensors described above with reference to FIGS. 1-2. As one example, a PCM (e.g., PCM 404 of FIG. 4) may include instructions for transmitting signals to other control modules of the control system (e.g., BCM 408 and HVAC controller 212 shown in FIG. 4) as well as instructions for receiving signals from the other control modules in order to execute method 500, as will be elaborated herein with respect to FIG. 7. The control system may employ actuators of the vehicle system to adjust vehicle system operation according to the methods described below. For example, the control system may utilize the control architecture shown in FIG. 4 to coordinate control of the HVAC system with operation of a powertrain.

At 502, method 500 includes estimating and/or measuring operating conditions. The operating conditions include vehicle, powertrain, and climate operating conditions. As an example, the vehicle conditions may include a status of each vehicle window and door (e.g., open or closed), a vehicle occupancy, a key fob proximity, a gear selection (e.g., determined from a gear selector, such as gear selector 108 of FIG. 1), a state of charge (SOC) of a system battery (e.g., energy storage device 150 of FIG. 1), and whether or not the vehicle is receiving power from an external power source (e.g., power source 180 of FIG. 1). As another example, the powertrain conditions may include an ignition status of an engine (e.g., engine 110 of FIGS. 1 and 2), an engine speed, an engine load, an amount of driver-demanded torque, an engine coolant temperature (e.g., determined from a signal received from engine coolant temperature sensor 211 of FIG. 2), cruise control settings, etc. As still another example, the climate operating conditions may include may include ambient temperature and humidity, a sun load of the vehicle, cabin temperature and humidity, etc. Still other operating conditions may include determining whether an AV mode is selected (e.g., when the vehicle is an autonomous vehicle including an AV controller, such as AV controller 191 of FIG. 1) and/or whether a car-sharing module is active (e.g., car-sharing module 193 of FIG. 1). For example, when the car-sharing module is active, the operating conditions may further include estimating a number of unique occupants that have entered the vehicle since the vehicle was last operated in the vehicle sanitizing mode, and thus adjusting or commencing the sanitizing mode in response to the number reaching a non-zero threshold of unique users and/or occupants, as will be elaborated below.

At 504, method 500 includes determining if the vehicle sanitizing mode is requested. The vehicle sanitizing mode may be requested by a vehicle operator (e.g., a user) via an input device, such as via an HMI (e.g., HMI 196 of FIG. 1), cruise control buttons (e.g., cruise control buttons 134 of FIG. 1), a smartphone app, hard/soft buttons, key fob buttons (e.g., key fob 195 of FIGS. 1 and 2), electronic door keypad buttons, or a pre-programmed combination of such inputs. As one example, the operator may input a pre-programmed pattern of cruise control button depressions, such as an order and combination of "on," "off," "set+," and "set−" button depressions. In other examples, the vehicle sanitizing mode may be automatically activated per a defined schedule, such as once daily at a pre-determined time, twice weekly at a pre-determined time, etc., such as will be elaborated below with respect to FIG. 10. In still other examples, the vehicle sanitizing mode may be automatically requested when a threshold number of unique occupants has entered the vehicle since the vehicle was last operated in the vehicle sanitizing mode. The threshold number of unique occupants refers to a pre-determined, non-zero number of occupants that may be calibrated to balance fuel, energy, and/or time costs of operating in the vehicle sanitizing mode with transmission rates and case numbers of prevalent infectious diseases, for example. Further, the vehicle sanitizing mode may be automatically initiated during autonomous occupant-free vehicle travel and/or operation.

In some examples, the vehicle sanitizing mode may be requested while the vehicle is operated in a secure idle mode, during which the vehicle remains running (e.g., in park, with the engine idling and electrical power provided to vehicle accessories, such as interior and exterior lights) while the key is removed from the ignition. For example, the secure idle mode may be selected by the operator via the HMI, a smartphone app, hard/soft buttons, or a key fob button prior to turning off the ignition and removing the key. In this way, the key may be removed from the vehicle for anti-theft purposes while the vehicle remains on. As such, the vehicle may enter the requested vehicle sanitizing mode while operating in the secure idle mode responsive to entry conditions being met, as will be elaborated below with respect to 506.

Further, in some examples, the request may include a type of vehicle sanitizing mode requested. For example, the types may include a deep clean mode, a quick clean mode, and the like. The deep clean mode may include different settings than the quick clean mode, for example, in order to more effectively sanitize the vehicle interior. As an example, the deep clean mode may eliminate substantially all heat-sensitive microbes in the vehicle interior, whereas the quick clean mode may significantly reduce a number of heat-sensitive microbes in the vehicle interior.

If the vehicle sanitizing mode is not requested, method 500 proceeds to 508 and includes maintaining the vehicle sanitizing mode inactive. For example, the vehicle sanitizing mode may be an automatic strategy that utilizes a state machine to track a status and progress of a sanitization routine, as will be elaborated with reference to FIG. 7. Thus, by maintaining the vehicle sanitizing mode in the inactive status, the sanitization routine will not be executed, and the powertrain and HVAC system will not be operated in the vehicle sanitizing mode.

At 526, method 500 includes operating the powertrain and the HVAC system in a nominal climate control mode. As will be elaborated with respect to FIG. 6, the nominal climate control mode may include determining powertrain and HVAC settings to achieve passenger-specified climate settings. Thus, the HVAC system is not used to provide heat sanitization to the vehicle interior. Method 500 may then end.

Returning to 504, if the vehicle sanitizing mode is requested, method 500 proceeds to 506 and includes determining if vehicle sanitizing mode entry conditions are met. The entry conditions may include, for example, the vehicle being in park, an indication that the vehicle is not occupied, the engine being on, the vehicle doors and windows being closed, and a fuel level being greater than a threshold fuel level. Because the engine may be used to produce heat for the sanitization routine, the threshold fuel level refers to a pre-calibrated non-zero fuel level below which there may not be enough fuel to complete the sanitization routine. In examples where several different vehicle sanitizing modes are included, the threshold fuel level may be different (e.g., higher) for the deep clean mode than the quick clean mode. In electric vehicles, an electric heater additionally or alternatively may be used to generate heat for the sanitization routine. Thus, in such examples, the entry conditions may include the battery SOC being greater than a threshold SOC, the threshold SOC referring to a pre-calibrated non-zero SOC below which there may not be enough electrical energy to complete the sanitization routine. Similar to the threshold fuel level, the threshold SOC may be different (e.g., higher) for the deep clean mode relative to the quick clean mode. All of the entry conditions may be confirmed for it to be determined that the vehicle sanitizing mode entry conditions are met.

If the vehicle sanitizing mode entry conditions are not met, method 500 proceeds to 508, as described above. Thus, even if the vehicle sanitizing mode is requested, the sanitization routine will not be executed unless the entry conditions are met. Thus, the powertrain and HVAC system will not be operated in the vehicle sanitizing mode when the vehicle is occupied, a door or window is open, there is not enough fuel (or battery SOC) to complete the sanitization routine, etc. Further, although not explicitly shown, if at any point the vehicle sanitizing mode entry conditions are no longer met, even after the vehicle sanitizing mode entry conditions are confirmed and the vehicle sanitizing mode is activated, method 500 may proceed to 508 to inactivate the vehicle sanitizing mode, as will be further elaborated below with respect to FIG. 7.

On the other hand, if the vehicle sanitizing mode entry conditions are met, method 500 proceeds to 510 and includes activating the vehicle sanitizing mode. Activating the vehicle sanitizing mode may include updating the state machine to an "active" status and entering the sanitization routine. Thus, the control system may commence operation in the vehicle sanitizing mode responsive to the vehicle sanitizing mode entry conditions being met when the vehicle sanitizing mode is requested (e.g., by the vehicle operator or according to other pre-programmed criteria).

In some examples, activating the vehicle sanitizing mode includes adjusting a position of a sun shade (e.g., sun shade 256 of FIG. 2) based on the sun load, as optionally indicated at 509. For example, 509 may be performed as a part of method 500 when the vehicle includes the sun shade. As described with respect to FIG. 2, the sun shade may be positioned with respect to a roof window (e.g., roof window 255) via a sun shade actuator (e.g., sun shade actuator 258) in order to block or enable light transmission through the roof window, with an amount of the light transmission increasing as the sun shade is further opened. Therefore, as one example, the sun shade may be adjusted to a further open position (e.g., when the sun shade is not in the fully open position) responsive to the sun load being greater than a threshold sun load. The threshold sun load may be a pre-determined, non-zero value above which it is expected that increased ambient light transmission and reduced thermal insulation at the roof window will increase the cabin temperature of the vehicle and below which it is expected that reduced thermal insulation at the roof window will decrease the cabin temperature of the vehicle. As another example, the threshold sun load may be adjusted based on the ambient temperature. For example, the threshold sun load may be decreased as the ambient temperature increases and increased as the ambient temperature decreases.

In some examples, the sun shade may be adjusted to the fully open position responsive to the sun load being greater than the threshold sun load and may be adjusted to a fully closed position responsive to the sun load being less than the threshold sun load. In other examples, the sun shade may be adjusted to a partially open (or partially closed) position between the fully open position and the fully closed position. As an example, the position of the sun shade may be directly determined based on one or more of the sun load and the ambient temperature, such as by the control system inputting the sun load and/or the ambient temperature into a look-up table, algorithm, or map stored in memory, which may output the corresponding position of the sun shade for the input conditions. The sun shade may then be adjusted to the output position via the sun shade actuator.

When the sun shade actuator is an electronic actuator, the control system may automatically position the sun shade to the determined position. When the sun shade actuator is a manual actuator, the controller may prompt the operator to position the sun shade to the determined position when the vehicle sanitizing mode is requested at 504, such as via a message communicated at the HMI or via a smartphone message, for example. Further, the control system may receive an indication from the operator (e.g., input via the HMI or the smartphone) that the sun shade has been adjusted to the determined position before proceeding in the vehicle sanitizing mode.

Activating the vehicle sanitizing mode optionally includes activating UV lights and/or an auxiliary heating system, as indicated at 511. For example, 511 may be performed as a part of method 500 when the vehicle includes at least one of a UVGI system, such as UVGI system 280 of FIG. 2, and the auxiliary heating system (e.g., auxiliary heating system 290 of FIG. 2).

When included, the UV lights (e.g., the plurality of UV light sources 281) may be activated by supplying electrical power to the UV lights, for example, causing the UV lights to emit light in the UV (e.g., UVC) range. As described above with respect to FIG. 2, the UV lights may irradiate vehicle surfaces, which may supplement the heat-cleaning of the vehicle sanitizing mode.

When the auxiliary heating system includes a fuel-operated parking heater, the auxiliary heating system may be activated by supplying fuel and air to the parking heater for combustion within the parking heater. In some examples, the controller may prompt the operator to activate the auxiliary heating system responsive to the vehicle sanitizing mode entry conditions being met at 506, such as via a smartphone message, for example. Further, the control system may receive confirmation from the operator (e.g., input via the smartphone) that the auxiliary heating system has been activated. By activating the auxiliary heating system, more heat may be generated than by using the powertrain and the HVAC system alone. As a result, a higher temperature may be reached and/or the temperature may be increased more quickly. At 512, method 500 includes operating the powertrain and the HVAC system in a heating cycle. As mentioned above, the sanitization routine may be divided into the heating cycle, a maintain cycle, and a cooldown cycle, with each of the heating cycle, the maintain cycle, and the cooldown cycle including specific settings for heat sanitization and subsequent cooling of the vehicle interior. The heating cycle occurs first, followed by the maintain cycle, which is then followed by the cooldown cycle.

The heating cycle settings are configured to rapidly produce heat for heat sanitization, which may be greater than an amount of heat produced during nominal powertrain and HVAC system operation. As one example, to operate in the heating cycle, the PCM increases the engine speed from a default idle speed set-point, such as to a higher idle speed set-point. For example, the heating cycle may include an idle air control setting that increases the idle speed set-point to 1500 rpm. Thus, more air and fuel may be delivered to the engine than during nominal engine idling outside of the vehicle sanitizing mode in order to increase the engine speed. If the engine includes an idle-stop feature that automatically shuts down the engine during idling, the idle-stop feature is deactivated. Further, the PCM turns off the engine cooling fan (e.g., engine cooling fan 92 of FIG. 2) in order to decrease cooling provided to the engine and increase the engine coolant temperature.

In some examples, the idle speed set-point may be adjusted based the climate operating conditions, such as the ambient temperature and the sun load of the vehicle, in order to produce a desired amount of heat for the heat sanitization. Further, the desired amount of heat may be different (e.g., higher) for the deep clean mode than for the quick clean mode. For example, when the ambient temperature is above a pre-defined temperature value, the ambient temperature may provide a portion of the desired amount of heat. Similarly, when the sun load is above a pre-defined sun load value, heat irradiated from the sun may provide a portion of the desired amount of heat. Therefore, as the ambient temperature and/or the sun load of the vehicle further increase above their respective pre-defined values, the idle speed set-point may be decreased in order to decrease the heat produced by the engine. Further, when the vehicle is an AV, the AV may move to a sunny parking spot having a high sun load responsive to the vehicle sanitizing mode being requested and prior to the vehicle sanitizing mode being activated in order to take advantage of the heat irradiated from the sun. Thus, the PCM may input the ambient temperature and the sun load into a look-up table, algorithm, or function, which may output the idle speed set-point to use for operating in the requested vehicle sanitizing mode.

In some examples, additional actions may be performed to increase the amount of heat produced by the engine while operating in the heating cycle, such as retarding a spark timing of an ignition spark to decrease an amount of torque produced for a same engine load, adding an accessory torque load (e.g., operating an alternator or generator to convert mechanical energy to electrical energy), closing grille shutters to reduce air flow through an engine compartment, engaging an auxiliary water pump (if available) to increase coolant flow through the engine and a heater core (e.g., heater core 90 of FIGS. 2 and 3), and decreasing coolant flow to components other than the heater core (e.g., by closing valves to transmission cooling circuits, oil coolers, etc.).

Additionally or alternatively, in an electric vehicle (e.g., a HEV or an electric-only powertrain), operating the powertrain in the heating cycle includes activating the electric heater, such as by supplying electric power to the electric heater from the battery, and engaging an electric motor (e.g., motor 120 of FIG. 1) against vehicle brakes to increase heat generation. Further, in some HEV examples, the engine may not be operated when the electric heater alone is able to generate enough heat to raise the cabin temperature to a desired temperature for heat sterilization, as will be elaborated below. For example, the PCM may decide whether or not to operate the engine based on a known heat output of the electric heater, the ambient temperature, and the sun load. Thus, when the heat output of the electric heater and an amount of heat provided by the ambient environment (e.g., determined from the ambient temperature and the sun load) is greater than the desired amount of heat for performing the heat sanitization, the engine may be turned off (or may remain off).

As another example, operating in the heating cycle may include the PCM transmitting instructions to the HVAC controller to operate the HVAC system with high heat settings. The high heat settings may include operating a blower (e.g., blower 308 of FIG. 3) at maximum speed in order to provide maximum air flow through the HVAC system, providing full heat, and operating with a floor mode selected. For example, to provide full heat, a blend door (e.g., blend door 332 of FIG. 3) may be maintained in a hot position. As another example, to operate with the floor mode selected, hot air may be selectively delivered to the vehicle cabin via ducting directed to the floor, and not to vents or panels (e.g., by positioning one or more delivery doors accordingly). As one example, the floor mode may be selected because it does not rely on the vehicle operator to open or position vent shutters/vanes. As another example, the floor mode may be selected for the heating cycle because it enables heat to naturally rise from the floor to the rest of the vehicle interior. The high heat settings may further include setting an air inlet door (e.g., air inlet door 306 of FIG. 3) to a recirculated air position while the engine coolant temperature remains less than a threshold engine coolant temperature (e.g., 100° C.). The recirculated air position enables the cabin air to be reheated as it is recirculated through the HVAC system. Responsive to the engine coolant temperature reaching or exceeding 100° C., the air inlet door may be adjusted to a fresh air position so that fresh air is drawn into the HVAC system. Further still, operating in the heating cycle may include activating any heated surfaces (e.g., heated surfaces 270 of FIG. 2), such as heated seats, a heated steering wheel, heated front window and rear window components, and any other radiant panels or fibers.

Further, in some examples, the vehicle control system may output an event-based message to the user, such as via a smartphone app or other interface, regarding the current status of operating in the heating cycle. The message may further include information regarding a percentage of the sanitization routine that has been completed, an estimated time to completion for the current cycle and/or the sanitization routine, a current cabin temperature, a real-time indication of the fuel level and/or battery state of charge, etc. As one example, the smartphone app or other interface may be connected to a Cloud-based wireless network or mobile phone service that is also connected to the control system of the vehicle, enabling the user to receive messages even when located remotely from the vehicle. In another example, the smartphone app may be directly connected to the control system via Wi-Fi, Bluetooth®, or another wireless technology, and thus, the user may be instructed to remain within a signal range for that wireless technology in order to receive updates and event-based messages.

At 514, method 500 includes determining if the cabin temperature is greater than or equal to a first threshold temperature. The cabin temperature may be measured by one or more cabin temperature sensors, such as cabin temperature sensors 218 of FIG. 2. Alternatively, a measurement from a different temperature sensor that gives an indication of the temperature of air in the vehicle cabin may be used, such as a discharge air temperature sensor or an evaporator temperature sensor. The first threshold temperature is a non-zero, positive temperature value and represents the lowest temperature for performing heat sanitization. For example, when exposed to temperatures at or above the first threshold temperature, microbes are expected to be killed or deactivated. Further, the first threshold temperature is greater than a nominal temperature range used for passenger comfort in the nominal climate control mode, as will be elaborated below with respect to FIG. 6.

In some examples, the first threshold temperature is a fixed value. For example, the fixed value may be 56° C. As another example, the fixed value may be 70° C. However, in other examples, the first threshold temperature may be adjusted based on the cabin humidity, as measured by a cabin humidity sensor (e.g., cabin humidity sensor 219). For example, as the cabin humidity increases, the first threshold temperature may decrease, as higher humidity may aid sanitization at lower temperatures. As one example, the PCM may input the measured cabin humidity into a look-up table, algorithm, or function, which may output the adjusted first threshold temperature (or adjustment to make to the fixed value) for the input cabin humidity. Additionally or alternatively, in some examples, the first threshold temperature may be adjusted based on the type of vehicle sanitizing mode requested. For example, the first threshold temperature may be higher for the deep clean mode and lower for the quick clean mode. However, in other examples, the first threshold temperature may be the same across all vehicle sanitizing modes.

If the cabin temperature is not greater than or equal to the first threshold temperature (e.g., the temperature is less than the first threshold temperature), method 500 returns to 512 and continues operating the powertrain and the HVAC system with the heating cycle settings. Thus, the powertrain and HVAC system may continue to be operated to rapidly produce heat and increase the cabin temperature, thereby increasing a temperature of interior vehicle surfaces for heat sanitization.

If the cabin temperature is greater than or equal to the first threshold temperature, method 500 proceeds to 516 and includes operating the powertrain and the HVAC in the maintain cycle. The maintain cycle is configured to maintain the cabin temperature at or above the first threshold temperature for a first threshold duration. The first threshold duration corresponds to a non-zero amount of time for heat sanitization to kill or deactivate microbes on the interior vehicle surfaces. In some examples, the first threshold duration may be a fixed amount of time, such as 15 minutes. In other examples, the first threshold duration may be adjusted based on based on the cabin humidity and/or whether or not the UV lights are activated. For example, as the cabin humidity increases, the first threshold duration may decrease, as higher humidity may increase a rate at which sanitization occurs. As one example, the PCM may receive the measured cabin humidity from the HVAC controller over the CAN, and the PCM may input the measured cabin humidity into a look-up table, algorithm, or function, which may output the adjusted first threshold duration (or an adjustment to make to the fixed amount of time) for the input cabin humidity. As another example, the first threshold duration may be longer when UV lights are not activated and shorter when UV lights are activated, as the UV lights may supplement the heat sanitization.

Additionally or alternatively, in some examples, the first threshold duration may be different for the different vehicle sanitizing mode types. For example, the first threshold duration may be longer for the deep clean mode and shorter for the quick clean mode. Thus, the deep clean mode may include settings and instructions for maintaining the cabin temperature at a higher temperature and/or for a longer duration than the quick clean mode in order to kill a greater number of microbes than the quick clean mode.

As one example, operating in the maintain cycle may be similar to operating in the heating cycle, as high heat continues to be generated and provided to the vehicle cabin. However, operating in the maintain cycle may additionally include tracking the amount of time that the cabin temperature remains at or above the first threshold temperature, such as by setting a timer for the first threshold duration. In some examples, the first threshold duration may be automatically extended or reset if the cabin temperature drops below the first threshold temperature while the timer is active, as will be elaborated below with respect to FIG. 7.

In some examples, operating in the maintain cycle at 516 may further include outputting an event-based message to the user regarding the current status of operating in the maintain cycle. Further, sanitization routine parameters, such as the percentage of the sanitization routine that has been completed, the estimated time to completion for the current cycle and/or the sanitization routine, the current cabin temperature, the real-time indication of the fuel level and/or battery state of charge, may continue to be updated in real-time via the smartphone app or other interface.

At 518, method 500 includes determining if success conditions are met. As one example, it may be determined that the success conditions are met, and thus the decontamination is successful, responsive to the timer elapsing. Additionally or alternatively, it may be determined that the success conditions are met responsive to the cabin temperature remaining above the first threshold temperature for the first threshold duration. As still another example, it may be determined that the success conditions are met responsive to a maximum duration being reached. The maximum duration may be 90 minutes, for example, and may correspond to a maximum amount of time for automatically extending the timer responsive to the cabin temperature decreasing below the first threshold temperature during the maintain cycle.

If the success conditions are not met, method 500 returns to 516 and continues operating the powertrain and the HVAC system in the maintain cycle. Thus, the vehicle cabin will continue to be heated, with the sanitization process continued. In contrast, if the success conditions are met, method 500 proceeds to 520 and includes operating the powertrain and the HVAC system in the cooldown cycle. The cooldown cycle includes settings configured to bring the powertrain, the HVAC system, and interior surface temperatures back down to temperatures within nominal ranges achieved while operating outside of the vehicle sanitizing mode. Further, the cooldown cycle is configured to gradually decrease the cabin temperature in order to prevent or reduce HVAC system degradation due to component warping, for example.

Operating the powertrain in the cooldown cycle includes reducing the engine speed to a lower, nominal idle speed set-point. For example, the cooldown cycle may include an idle air control setting that decreases the idle speed set-point to a value within a range from 900-1100 rpm. As a result, the heat generated by the engine is reduced. Further, operating in the cooldown cycle includes turning on the engine cooling fan, which further decreases the engine coolant temperature, and thus, the heat transferred to air directed to the cabin via the HVAC system. Additionally or alternatively, in an electric vehicle, the electric heater is deactivated (e.g., electric power is no longer supplied to the electric heater), and the electric motor is disengaged. In vehicles that include the auxiliary heating system, the auxiliary heating system is deactivated, such as by no longer supplying fuel to the parking heater to discontinue combustion. Further, the heated surfaces may be deactivated such that heat is no longer generated. Further, when included, the UV lights may be deactivated to no longer irradiate the interior vehicle surfaces.

Operating the HVAC system in the cooldown cycle comprises a series of timed adjustments. First, the HVAC system is operated with the air inlet door in the fresh air position, the blower set to maximum speed, and the blend door in the hot position, as in the heat cycle (and maintain cycle). Further, air flow may continue to be provided via the floor mode. After a first set duration of time (e.g., 2 minutes), the blend door may be adjusted to a position that is midway between the hot position and a cold position in order to provide a half and half mix of hot air and cold air. After operating with the blend door at the midway position for a second set duration of time (e.g., 1 minute), the blend door may be further adjusted to the cold position in order to provide substantially only cold air (and no hot air) to the vehicle cabin. Further, air flow may be provided via a combination of a panel mode and the floor mode. Further still, air conditioning components of the HVAC system may be engaged. For example, an evaporator core (e.g., evaporator core 312 of FIG. 3) and a compressor (e.g., compressor 340 of FIG. 3) may be activated in order to reduce the temperature of the air provided to the vehicle cabin from the ambient temperature. Additionally, any heated surfaces (e.g., seats, the steering wheel, and windows) may be turned off.

Further, in some examples, the vehicle control system may output an event-based message to the user regarding the current status of operating in the cooldown cycle, with the sanitization routine parameters updated in real-time via the smartphone app or other interface.

At 522, method 500 includes determining if the cooldown cycle is complete. As one example, it may be determined that the cooldown cycle is complete responsive to the cabin temperature decreasing to a second threshold temperature. The second threshold temperature is a non-zero, positive temperature value that is less than the first threshold temperature and corresponds to a temperature below which a vehicle occupant may re-enter the vehicle without significant discomfort. Additionally or alternatively, the cooldown cycle may be considered to be complete after a second threshold duration has elapsed while operating in the cooldown cycle. The second threshold duration refers to an amount of time over which the vehicle interior is expected to cool to a temperature that allows vehicle occupant re-entry. The second threshold duration may be fixed (e.g., 10 minutes) or may be adjusted based on, for example, the ambient temperature and/or the sun load of the vehicle. For example, as the ambient temperature and/or the sun load of the vehicle decrease, the second threshold duration may decrease, as the lower ambient temperature and/or sun load may cause the vehicle interior to cool faster. As one example, the PCM may input the measured ambient temperature and/or sun load, received from the HVAC controller over the CAN, into a look-up table, algorithm, or function, which may output the adjusted second threshold duration (or adjustment to make to the fixed amount of time) for the input ambient temperature and/or sun load.

If the cooldown cycle is not complete, method 500 returns to 520 and continues operating the powertrain and the HVAC system with the cooldown cycle settings. Once the cooldown cycle is complete, method 500 proceeds to 524 and includes outputting a completion notification and inactivating the vehicle sanitizing mode. The completion notification may be output via interior or exterior lights, a human-machine interface (e.g., instrument cluster), and/or via a smartphone notification (e.g., an event-based message to the smartphone app). Further, the completion notification may be one of a successful completion notification or an unsuccessful completion notification. The successful completion notification and the unsuccessful completion notification may include different outputs to communicate to the user whether the vehicle sanitizing mode was completed successfully or not. As one example, the successful completion notification may include a single long pulse from the exterior lights (e.g., exterior lights 235 of FIG. 2), while the unsuccessful completion notification may include three short pulses from the exterior lights.

The successful completion notification is triggered responsive to the successful completion of each of the heating cycle, the maintain cycle, and the cooldown cycle, while the unsuccessful completion notification may be triggered responsive to the sanitization routine being cancelled or aborted prior to completing all of the heating cycle, the maintain cycle, and the cooldown cycle. Additionally or alternatively, the unsuccessful completion notification may be triggered responsive to the vehicle sanitizing mode entry conditions not being met at 506 (or not remaining met while the sanitization routine is executed). As still another example, the unsuccessful completion notification may be triggered responsive to the first threshold temperature not being achieved within the maximum duration.

Method 500 may then proceed to 526 to operate the powertrain and the HVAC system in the nominal climate control mode. Continuing to FIG. 6, an example method 600 is provided for operating in the nominal climate control mode. As an example, method 600 may be performed as a part of method 500 (e.g., at 526). As another example, method 600 may be executed responsive to receiving a request to activate the HVAC system whenever the vehicle is operated. For example, the nominal climate control mode may be a default mode, and the HVAC system may only be operated out of the default mode (e.g., in the vehicle sanitizing mode) responsive to the vehicle sanitizing mode being requested at 504 of FIG. 5.

At 602, method 600 includes estimating vehicle climate conditions. The vehicle climate conditions may include the cabin temperature and humidity, the vehicle sun load, the ambient temperature and humidity, the air quality, etc. The vehicle climate conditions may further include the position of the sun shade, which may be adjusted responsive to user input (and not automatically based on the sun load relative to the threshold sun load) while operating in the nominal climate control mode. For example, the user may directly control the position of the sun shade via the manual or electronic sun shade actuator.

At 604, method 600 includes determining passenger-specified climate conditions. The passenger-specified climate conditions may be determine based on inputs from a vehicle occupant (e.g., driver or passenger) on a climate-control interface (e.g., climate-control interface 242 of FIG. 2) and may include settings or set-points for a level of thermal comfort desired in the cabin space. For example, the passenger-specified climate conditions may indicate a desired amount of heating or cooling of the cabin space, including a temperature set-point. The temperature set-point may be constrained to the nominal temperature range, as mentioned above with respect to FIG. 5. The nominal temperature range includes temperatures that are less than the first threshold temperature described at 514 of FIG. 5. Thus, the vehicle occupant may not directly select a temperature set-point, including the first threshold temperature, that is outside of the nominal temperature range. As one example, the nominal temperature range may extend between approximately 15 and 25° C.

Additionally, a direction of air flow may be specified, such as directed toward the floor of the vehicle (e.g., via the floor mode), toward the passenger seats (e.g., via a vent mode), and/or toward panels in the interior of the vehicle (e.g., via the panel mode). The passenger-specified climate conditions may also specify a rate of air flow (for example, low, medium or high flow rates). Further, the settings may specify a ratio of fresh air (from outside the vehicle) to recirculated air (from inside the vehicle).

Additionally or alternatively, the passenger-specified climate conditions may include preconditioning climate conditions. The preconditioning may be plug-in preconditioning performed in an EV or plug-in HEV. As will be elaborated below with respect to FIG. 10, the preconditioning climate conditions may include specified climate conditions that are set ahead of time (e.g., prior to the vehicle being operated). As one example, the preconditioning climate conditions may include a cabin preconditioning temperature set-point and a pre-set time for executing the preconditioning, both the cabin preconditioning temperature set-point and the pre-set time input by the user (e.g., the driver or other occupant) via a preconditioning app (e.g., software application) accessed via a user interface, such as HMI 196 of FIG. 1 or smartphone 295 of FIG. 2. As one example, the control system may set an alarm wake up or timer for the pre-set time, and upon reaching the pre-set time, the control system may wake up from a sleep mode without additional user input to raise the cabin temperature to the cabin preconditioning temperature set-point by activating the electric heater.

In some examples, the preconditioning may only be performed while the vehicle is receiving electrical power from the external power source, which may be used to power the electric heater instead of the energy storage device. In other examples, the preconditioning may also be performed while the vehicle is not receiving electrical power from the external power source, such as responsive to the SOC of the battery being greater than a second threshold SOC. The second threshold SOC may refer to a battery SOC below which the battery may not have enough charge to support vehicle usage following the preconditioning. Additionally or alternatively, a modified version of the preconditioning may be performed when the vehicle is not receiving electrical power from the external power source, such as by raising the cabin temperature to a value that is a pre-defined amount less than the cabin preconditioning temperature set-point or performing the cabin temperature until the battery SOC decreases to a pre-set SOC.

In a further example, additionally or alternatively, the passenger-specified climate conditions may include settings for the auxiliary heating system. For example, the user may indicate whether to use the auxiliary heating system as well as a temperature set-point of the auxiliary heating system. In some examples, the auxiliary heating system may only be used while the vehicle is parked, such as when the auxiliary heating system includes the parking heater.

At 606, method 600 includes determining powertrain and HVAC system settings to achieve the passenger-specified climate conditions given the vehicle climate conditions. Determining the powertrain settings may include, for example, determining an idle air control setting, such as increasing the idle air control setting to increase an amount of heat output by the engine in response to a higher temperature set-point relative to the ambient temperature and sun load of the vehicle. As another example, determining the powertrain settings may include determining a speed of the engine cooling fan, such as decreasing the speed responsive to a higher temperature set-point relative to the ambient temperature and sun load of the vehicle. Determining the HVAC system settings may include, for example, determining a ratio of hot air to cold air to be generated by HVAC system heating and cooling elements respectively (including a setting for activating the electric heater, when included), and/or a ratio of fresh air to recirculated air to be mixed into the air flow. For example, the HVAC controller may determine a position of the blend door and a position of the air inlet door accordingly. Determining the HVAC system settings may further include, for example, determining a rate and direction of the air flow. For example, the HVAC controller may determine the blower speed and a position of one or more delivery doors. When the parking heater is used, method 600 may further determine a motor fan speed and a fuel metering pump speed or (pulse-width of activation) to use for producing the temperature set-point of the auxiliary heating system.

At 608, method 600 optionally includes adjusting powertrain operation based on the determined powertrain settings. For example, if the determined powertrain settings are different than currently used powertrain settings, the powertrain operation may be adjusted, such as by increasing the engine idle speed to the higher idle air control setting and/or decreasing the engine cooling fan speed, for example. Alternatively, if the powertrain is already operating with the determined powertrain settings (e.g., the nominal idle air control setting and engine cooling fan speed are adequate to produce the passenger-specified climate conditions), the powertrain operation is maintained, and 608 is omitted.

At 610, method 600 includes operating the HVAC system based on the determined HVAC system settings. For example, the blend door, the air inlet door, and the delivery door(s) may all be actuated to the determined positions. Additionally, the blower may be operated at the determined speed. When cooling is requested, such as when the temperature set-point is less than the ambient temperature and/or an air-conditioning mode is selected, the evaporator core and the compressor may be activated. Alternatively, when heating is requested, such as when the temperature set-point is greater than the ambient temperature and/or a heating mode is selected, the evaporator core and the compressor may be deactivated. Further, in electric vehicle embodiments, the electric heater may be activated responsive to heating being requested. Method 600 then ends.

In this way, a powertrain and an HVAC system of a vehicle may be operated differently when providing climate control for passenger comfort (e.g., operating in a nominal climate control mode) or providing heat sanitization (e.g., operating in a vehicle sanitizing mode). By using powertrain and/or HVAC system components to generate more heat than used for climate control, heat-sensitive microbes may be effectively killed. Further, by adjusting powertrain and/or HVAC system settings based on vehicle climate conditions, such as an ambient temperature and a sun load of the vehicle, fuel and/or electric energy consumption may be reduced. By exposing an entire vehicle cabin to heat sanitization via hot air generated by the powertrain and the HVAC system during the vehicle sanitizing mode, the vehicle cabin may be more effectively decontaminated than when chemical sanitizers are used. For example, hot air may easily reach between seats and other hard-to-reach areas that manual cleaning may miss. Further, UV lights may provide additional germicidal irradiation to the hard-to-reach areas. As a result, pathogen transmission from interior vehicle surfaces may be reduced.

Next, FIG. 7 shows an example block diagram of a control system 700 that may be used to provide heat sanitization to a vehicle cabin, such as by executing the method of FIG. 5. Note that control system 700 is one example of the execution of method 500 of FIG. 5. Components of FIG. 7 that function the same as components of FIGS. 1-4 are numbered the same and may not be re-introduced. Further, control system 700 will be described with respect to a powertrain comprising an engine, although control system 700 may be adapted for electric-only and HEV powertrains. Control system 700 includes PCM 404, BCM 408, and HVAC controller 212 communicating over a CAN (e.g., CAN 406 of FIG. 4). As shown, PCM 404 includes a CAN communication driver 734 for outputting communications over the CAN. PCM 404 stores a vehicle sanitizing mode feature 708, which may be a software feature stored as executable instructions on a memory of PCM 404. Vehicle sanitizing mode feature 708 includes a state machine 710. State machine 710 includes an initiate trigger 712, an inactive state 714, a heating phase 716, a maintain phase 718, and a success (e.g., cooldown) phase 720. Heating phase 716, maintain phase 718, and success phase 720 are all active states with independent functions and transitions specified by the programmed instructions of vehicle sanitizing mode feature 708.

Further, vehicle sanitizing mode feature 708 outputs a signal that is a vehicle-level indication of the state of state machine 710 over the CAN via CAN communication driver 734. This signal may be received by HVAC controller 212 and BCM 408. In some examples, the signal may also be received by other control modules communicatively coupled to the CAN.

PCM 404, and thus vehicle sanitizing mode feature 708, receives a pedal/PRNDL input 722. Pedal/PRNDL input 722 may include both input regarding a state of a pedal, such as pedal 192 of FIG. 1, and a gear selector (e.g., gear selector 108 of FIG. 1). PCM 404 also receives an input from cruise control buttons 134 and a cabin temperature, which may be communicated to PCM 404 from HVAC controller 212 over the CAN. In an alternative example, the input may be provided via another user interface (e.g., HMI 196 of FIG. 1 or smartphone 295 of FIG. 2) instead of cruise control buttons 134. Additional inputs to vehicle sanitizing mode feature 708 may be monitored and provided by an I/O signal feature source 732 and may include an engine temperature, an engine speed, an ignition state, a vehicle speed, and a fuel level. I/O signal feature source 732 may also monitor and provide pedal/PRNDL input 722, at least in some examples.

A sequence of programmed inputs directly input to PCM 404 or communicated to PCM 404 over the CAN (e.g., an activation sequence) comprise the initiate trigger 712. As an example, the sequence of programmed inputs may include an order and length of button presses of cruise control buttons 134. Recognition of the sequence may time out after a calibratable amount of time if the sequence is not completed within the calibratable amount of time. If the sequence is not recognized (e.g., due to timing out or the sequence being incorrect), no action is taken, and inactive state 714 is maintained at state machine 710.

Further, even if initiate trigger 712 is obtained, vehicle sanitizing mode feature 708 may abort, and state machine 710 may exit to inactive state 714, if the pedal/PRNDL input 722 indicates the gear selector is moved from park and/or the pedal is depressed. Further, vehicle sanitizing mode feature 708 may abort responsive to the ignition state being changed (e.g., the vehicle is turned off), the engine being turned off, or the vehicle speed increasing above zero, as indicated by I/O signal feature source 732. As still another example, vehicle sanitizing mode feature 708 may abort responsive to additional cruise control button depressions received via cruise control buttons 134. As a further example, vehicle sanitizing mode feature 708 may abort responsive to degradation in any of the sensors used in monitoring, such as an engine coolant temperature sensor, a cabin temperature sensor, etc., and/or responsive to degradation of any engine cooling system or HVAC system component (e.g., engine cooling fan 92 of FIG. 2). In still further examples, vehicle sanitizing mode feature 708 may abort responsive to any detected idle air control degradation, such as degradation of an electric throttle, and/or responsive to any CAN communication degradation.

Inactive state 714 may provide an "off" state of vehicle sanitizing mode feature 708 and may be communicated to other modules, such as BCM 408 and HVAC controller 212, so that related functions may be coordinated. State machine 710 may remain at inactive state 714 until initiate trigger 712 is received or if any of the above-described abort conditions are present. In contrast, state machine 710 may transition to heating phase 716 responsive to receiving initiate trigger 712 and while none of the abort conditions are present. However, as mentioned above, state machine 710 may transition back to inactive state 714 responsive to any abort condition being present even after entering heating phase 716.

Heating phase 716 provides programmed settings for increasing the engine coolant temperature, and thus an amount of heat transferred to air provided to the vehicle cabin. PCM 404 communicates the heating phase 716 state to other modules, including HVAC controller 212, via the CAN (e.g., "heat_mode_active") in order to increase the cabin temperature. Further, vehicle sanitizing mode feature 708 communicates the heating phase 716 state to an idle air controller (IAC) 726 in order to increase an idle speed of the engine to a heating set-point speed (e.g., to 1500 rpm), to an electric drive fan controller (EDF) 728 in order to shut off the engine cooling fan, and to an air-conditioning compressor (ACC) 730 in order to deactivate the air-conditioning compressor (e.g., compressor 340 of FIG. 3). For example, EDF 728 may maintain the engine cooling fan deactivated, with a speed of zero, unless the engine coolant temperature increases above a calibratable engine coolant temperature threshold, an exhaust temperature increases above a calibratable exhaust temperature threshold, or a transmission oil temperature increases above a calibratable transmission oil temperature. Heating phase 716 may further include programmed settings for UVGI system 280, when applicable. For example, the programmed settings may include an intensity of light to emit from light sources of the UVGI system 280.

State machine 710 transitions from heating phase 716 to maintain phase 718 once heating phase 716 is completed. Heating phase 716 is considered completed when the cabin temperature is above a calibrated threshold (e.g., the first threshold temperature described above at 514 of FIG. 5) and no abort condition is present. Conversely, state machine 710 transitions to inactive state 714 if heating phase 716 does not complete within a maximum calibratable time threshold (e.g., the maximum duration described above with respect to FIG. 5) or if an abort condition is present. The heat-generating settings used in heating phase 716 may be maintained in maintain phase 718. For example, maintain phase 718 provides a strategy for holding an elevated engine coolant temperature. PCM 404 communicates the maintain phase 718 state to other modules, including HVAC controller 212, via the CAN (e.g., "heat_mode_active") in order to maintain the elevated cabin temperature. The heat-generating settings used in heating phase 716 may be maintained in maintain phase 718. For example, maintain phase 718 provides a strategy for holding the elevated engine coolant temperature. PCM 404 communicates the maintain phase 718 state to other modules, including HVAC controller 212, via the CAN (e.g., "heat_mode_active") in order to maintain the elevated cabin temperature. For example, maintain phase 718 may provide a maintenance timer.

Further, state machine 710 may transition from maintain phase 718 back to heating phase 716 responsive to the cabin temperature decreasing below the calibrated threshold by more than a hysteresis value for more than a calibratable amount of time. If state machine 710 returns to heating phase 716 and then re-enters maintain phase 718, the maintenance timer may be reset, with a number of maintenance timer resets logged. If the number of maintenance timer resets exceeds a calibratable amount, state machine 710 may abort to inactive state 714.

State machine 710 transitions from maintain phase 718 to success phase 720 once maintain phase 718 is completed. Maintain phase 718 is considered completed when the cabin temperature remains above the calibrated threshold for a calibrated amount of time (e.g., the first threshold duration described above at 516 of FIG. 5) and no abort condition is present. Conversely, state machine 710 transitions to inactive state 714 if maintain phase 718 does not complete within the maximum calibratable time threshold or if an abort condition is present.

Success phase 720 provides a state where the vehicle sanitization has been completed. Success phase 720 is also used to cool down the engine coolant and HVAC system components. PCM 404 communicates the success phase 720 state to other modules, including HVAC controller 212, via CAN communication driver 734 in order to reduce the cabin temperature. Further, vehicle sanitizing mode feature 708 communicates the success phase 720 state to IAC 726 in order to reduce the idle speed of the engine, to EDF 728 in order to turn on the engine cooling fan at maximum speed, for example, and to ACC 730 in order to activate the air-conditioning compressor. Further, HVAC component settings communicated to HVAC controller 212 may be adjusted over time in order to provide gradual cooling, as described above with respect to 520 of FIG. 5. For example, vehicle sanitizing mode feature 708 may request that the air-conditioning compressor be turned on after a calibrated amount of time.

State machine 710 transitions to inactive state 714 responsive to completion of success phase 720. Success phase 720 may be considered completed when the system state has been at success phase 720 for at least a calibratable threshold amount of time (e.g., the second threshold duration described at 522 of FIG. 5). For example, success phase 720 may provide a cooldown timer.

Further, PCM 404 may track diagnostics and other statistics regarding vehicle sanitizing mode feature 708 in non-transitory memory, including a total number of times a heating cycle has been started (e.g., defined as state machine 710 transitioning from inactive state 714 to heating phase 716 upon recognition of initiate trigger 712), a total number of times a heating cycle has been fully completed (e.g., defined as state machine 710 transitioning from heating phase 716 to maintain phase 718, and then transitioning from maintain phase 718 to success phase 720), and any degradation or condition that caused state machine 710 to abort from any other state to inactive state 714.

Further, PCM 404 may communicate with an HMI or other interface 724 (e.g., a smartphone app) throughout the execution of vehicle sanitizing mode feature 708. In some examples, HMI or other interface 724 may display or communicate a commencement of vehicle sanitizing mode feature 708, a progress through state machine 710, and a completion of vehicle sanitizing mode feature 708 through a combination of audible and/or visual cues (or indications). Other modules, such as BCM 408, may be responsible for at least some of the audible and/or visual cues, such as by controlling a pulse number and timing of exterior or interior light blinks.

Figure 8A:
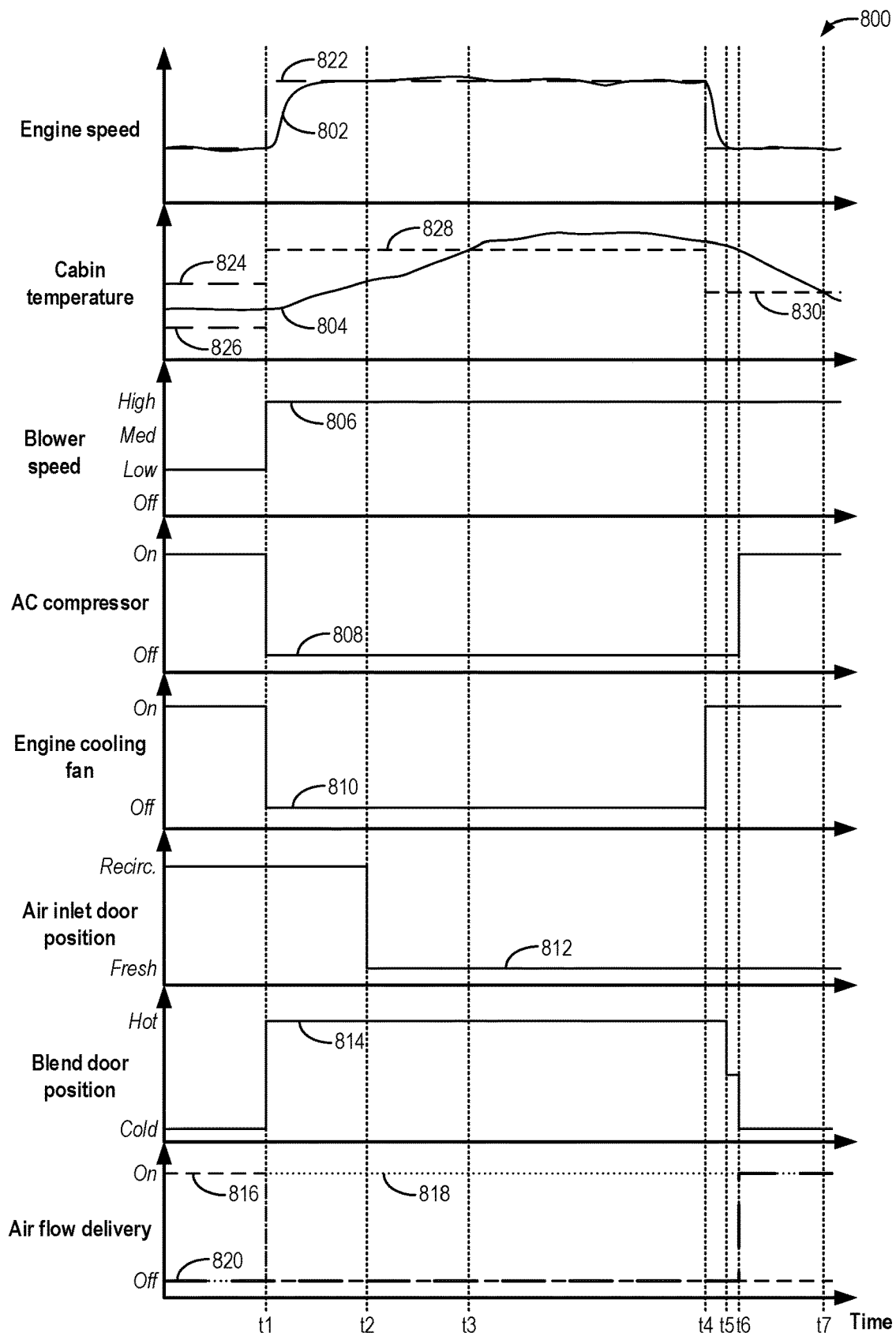
FIGS. 8A and 8B show a first prophetic example timeline for adjusting operation of a vehicle climate control system to perform heat sanitization.
Figure 8B:
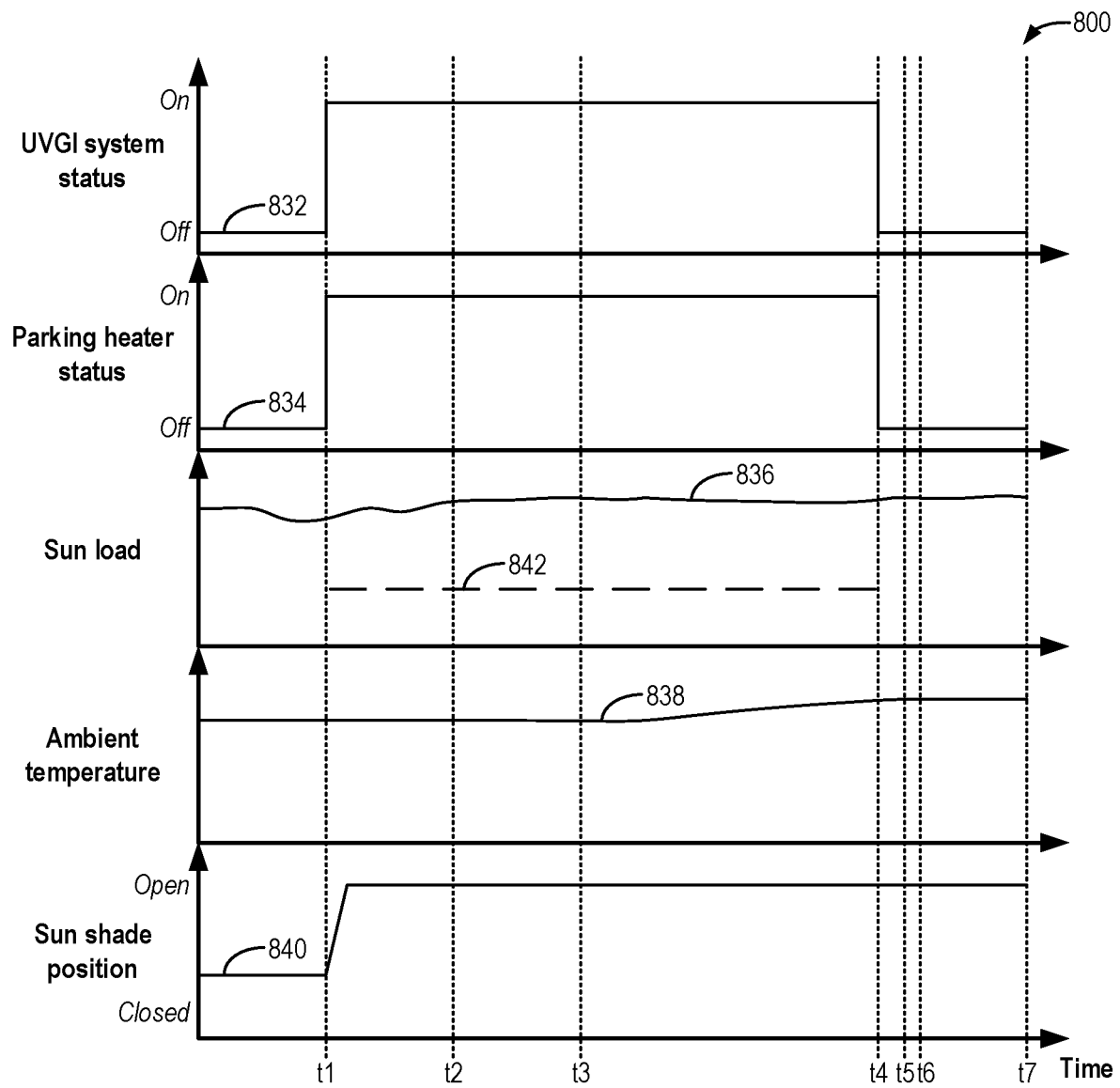

Next, FIGS. 8A and 8B show a first example timeline 800 for adjusting powertrain and HVAC system operation to operate in a vehicle sanitizing mode, such as particularly described above with reference to FIGS. 5 and 7. Engine speed is shown in a plot 802, a cabin temperature is shown in a plot 804, a blower speed is shown in a plot 806, an air-conditioning compressor status is shown in a plot 808, an engine cooling fan status is shown in a plot 810, an air inlet door position is shown in a plot 812, a blend door position is shown in a lot 814, an air flow delivery status of a vent mode is shown in a short-dashed plot 816, an airflow delivery status of a floor mode is shown in a dotted plot 818, an airflow delivery status of a panel mode is shown in a long-dashed plot 820, a UVGI system status is shown in a plot 832, a parking heater status is shown in a plot 834, a sun load is shown in a plot 836, an ambient temperature is shown in a plot 838, and a sun shade position is shown in a plot 840.

For all of the above, the horizontal axis represents time, with time increasing along the horizontal axis from left to right. The vertical axis represents each labeled parameter. For plots 802, 804, 836, and 838, a magnitude of the labeled parameter increases along the vertical axis from bottom to top. For plot 806, the vertical axis shows the blower speed setting as "off" (e.g., a speed of zero), "low," "medium," or "high." For plots 808, 810, 832, and 834, the vertical axis indicates whether the corresponding component is "on" (e.g., active) or "off" (e.g., inactive). For plot 812, the vertical axis shows the air inlet door position ranging from a recirculated air position ("recirc."), at which air is recirculated through the HVAC system from the vehicle cabin, and a fresh air position ("fresh"), at which air is drawn into the HVAC system from outside the vehicle. For plot 814, the blend door position is shown ranging from a hot position ("hot"), at which only hot air is provided to the vehicle cabin, and a cold position ("cold"), at which only cold air is provided to the vehicle cabin. For plots 816, 818, and 820, the vertical axis shows whether the corresponding air flow delivery mode is "on" (e.g., providing air flow to the cabin) or "off" (e.g., not providing air flow to the cabin). For plot 840, the position of the sun shade is shown with respect to a fully open position ("open") and a fully closed position ("closed").

Further, an engine idle speed setting is shown by a dashed line 822, a nominal climate control temperature range is shown by dashed lines 824 and 826 (dashed line 824 defining an upper threshold temperature of the nominal climate control temperature range and dashed line 826 defining a lower threshold temperature of the nominal climate control temperature range), a sanitization threshold temperature is shown by a dashed line 828, a cooldown threshold temperature is shown by a dashed line 830, and a sun load threshold is shown by a dashed line 842. Note that timeline 800 gives one illustrative example of the sanitization threshold temperature and the cooldown threshold temperature relative to the nominal climate control temperature range. In other examples, the cooldown threshold temperature may be higher than the upper threshold temperature of the nominal climate control temperature range, for example. However, it may be understood that the nominal climate control temperature range may not overlap with the sanitization threshold temperature.

Prior to time t1, the vehicle is operated in a nominal climate control mode. The engine is idling, with the engine speed (plot 802) at a lower engine idle speed setting (dashed line 822). Further, the engine cooling fan is on and operating at a non-zero speed (plot 810). The cabin temperature (plot 804) is maintained within the nominal climate control temperature range according to inputs received from a vehicle operator. In the example shown, based on the relatively high ambient temperature (plot 838) and the received inputs, the blower is operated at the low speed setting (plot 806), the AC compressor is on to provide air-conditioning (plot 808), the air inlet door is in the recirculated air position in order to provide recirculated air (plot 812), the blend door is positioned to provide fully cold air (plot 814), and the air flow is delivered to the cabin via vents. Thus, the vent mode is on (plot 816), while the floor more (plot 818) and the panel mode (plot 820) are off. Further, the sun shade is positioned at a partially open position that is closer to the fully closed position than the fully open position (plot 840). For example, due to the relatively high sun load (plot 836), the vehicle operator may have positioned the sun shade to allow some light in through a roof window while preventing glare. Further still, the parking heater is off, as auxiliary heating is not needed to warm the engine and cabin.

At time t1, the vehicle enters the vehicle sanitizing mode in response to an input received from the vehicle operator. A state machine of the vehicle sanitizing mode is transitioned to a heating phase, and the powertrain and HVAC system are operated with the corresponding heating phase settings. In particular, the engine idle speed setting is increased (dashed line 822), and engine operation is adjusted to increase the engine speed to the higher engine idle speed setting (plot 802). For example, additional air and fuel are supplied to the engine to increase the engine speed. Further, the engine cooling fan is commanded off (plot 810) in order to decrease engine cooling, thereby increasing an engine coolant temperature to a higher engine coolant temperature set-point, and thus, an amount of heat transferred to air via a heater core of the HVAC system. The blend door is adjusted to the hot position (plot 814) so that no cold air is included in the air flow provided to the cabin, and the air-conditioning compressor is turned off (plot 808). Further, the blower speed is increased to the high (e.g., maximum) setting (plot 806), and air flow is provided to the cabin via the floor mode only. That is, the floor mode is turned on (plot 818), the vent mode is turned off (plot 816), and the panel mode is maintained off (plot 820). As a result the cabin temperature begins to increase (plot 804).

Further still, at time t1, the UVGI system is activated (plot 832) to irradiate cabin surfaces with germicidal UV light, and the parking heater is turned on to provide auxiliary heat (plot 834). The control system determines the threshold sun load (dashed line 842) based on the ambient temperature (plot 838), and because the sun load (plot 836) is greater than the threshold sun load, the sun shade is adjusted to the fully open position (plot 840) to increase an amount of heat and light transferred from the ambient environment to the cabin via the roof window.

At time t2, the engine coolant temperature reaches a threshold temperature (not shown). In response, the air inlet door position is adjusted from the recirculated air position to the fresh air position (plot 812).

At time t3, the cabin temperature (plot 804) reaches the sanitization threshold temperature (dashed line 828). In response, the state machine is transitioned to a maintain phase, which tracks a duration of time at which the cabin temperature (plot 804) remains above the sanitization threshold temperature (dashed line 828). As shown, the sanitization threshold temperature is a maximum threshold temperature used for the cabin temperature.

At time t4, the duration tracked by the maintain phase reaches a threshold duration, and heating is considered complete. Further, vehicle sanitization is considered successful, and the state machine transitions to a cooldown (or success) phase. To transition to the cooldown phase, the engine idle speed setting is decreased to the nominal idle speed setting used prior to entering the vehicle heating mode (dashed line 822), and the engine speed is decreased accordingly (plot 802). Further, the engine cooling fan is turned on (plot 810). The UVGI system (plot 832) and the parking heater (plot 834) are both deactivated. As such, the UVGI system will no longer irradiate the cabin surfaces, and the parking heater will no longer supply auxiliary heat to the cabin and engine.

At the beginning of the cooldown phase (e.g., beginning at time t4), the blend door remains fully at the hot position (plot 812), the air inlet door remains at the fresh air position (plot 812), the blower speed remains at the high setting (plot 806), and the air flow continues to be provided to the cabin only via the floor mode (plot 818). However, because additional heat is no longer generated by the engine, the cabin temperature begins to decrease (plot 804).

At time t5, which occurs after a first amount of time of operating in the cooldown phase, the blend door position is adjusted to be halfway between the hot position and the cold position (plot 814). Further, at time t6, which occurs after a second amount of time of operating in the cooldown phase, the blend door position is further adjusted to the cold position (plot 814), and the air-conditioning compressor is turned on (plot 808). Further, the panel mode is turned on (plot 820) so that air flow is provided to the cabin via both the panel mode and the floor mode (and not the vent mode).

At time t7, the cabin temperature (plot 804) decreases to the cooldown threshold temperature (dashed line 830). As a result, the vehicle sanitizing mode is considered to be completed, and the state machine transitions to an inactive state. Thus, following time t7, the HVAC system is operated in the nominal climate control mode responsive to inputs from the vehicle operator. In some examples, the sun shade position may be adjusted back to the position it was in prior to operating in the vehicle sanitizing mode (e.g., the sun shade position prior to time t1.

Figure 9A:
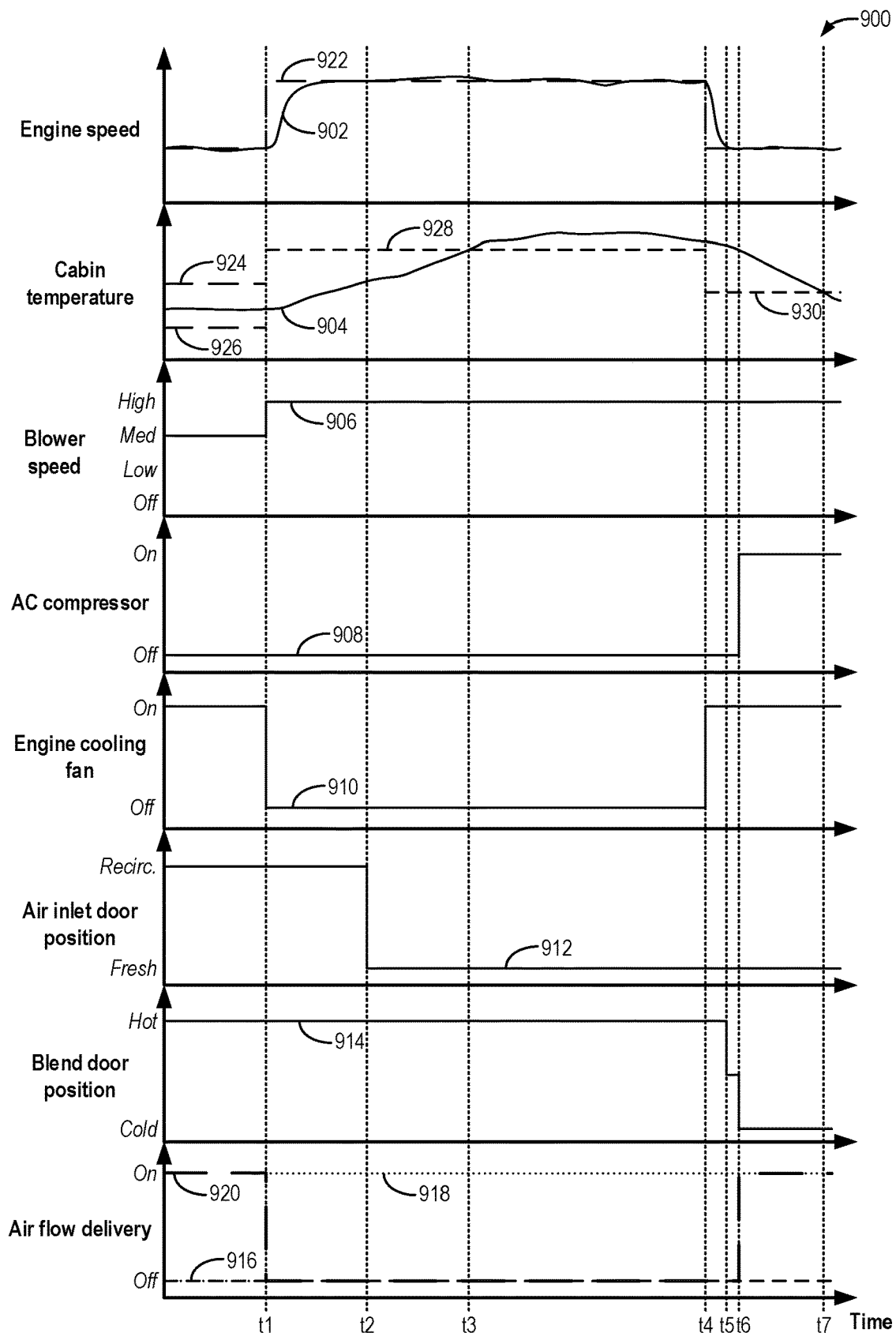
FIGS. 9A and 9B show a second prophetic example timeline for adjusting operation of a vehicle climate control system to perform heat sanitization.
Figure 9B:
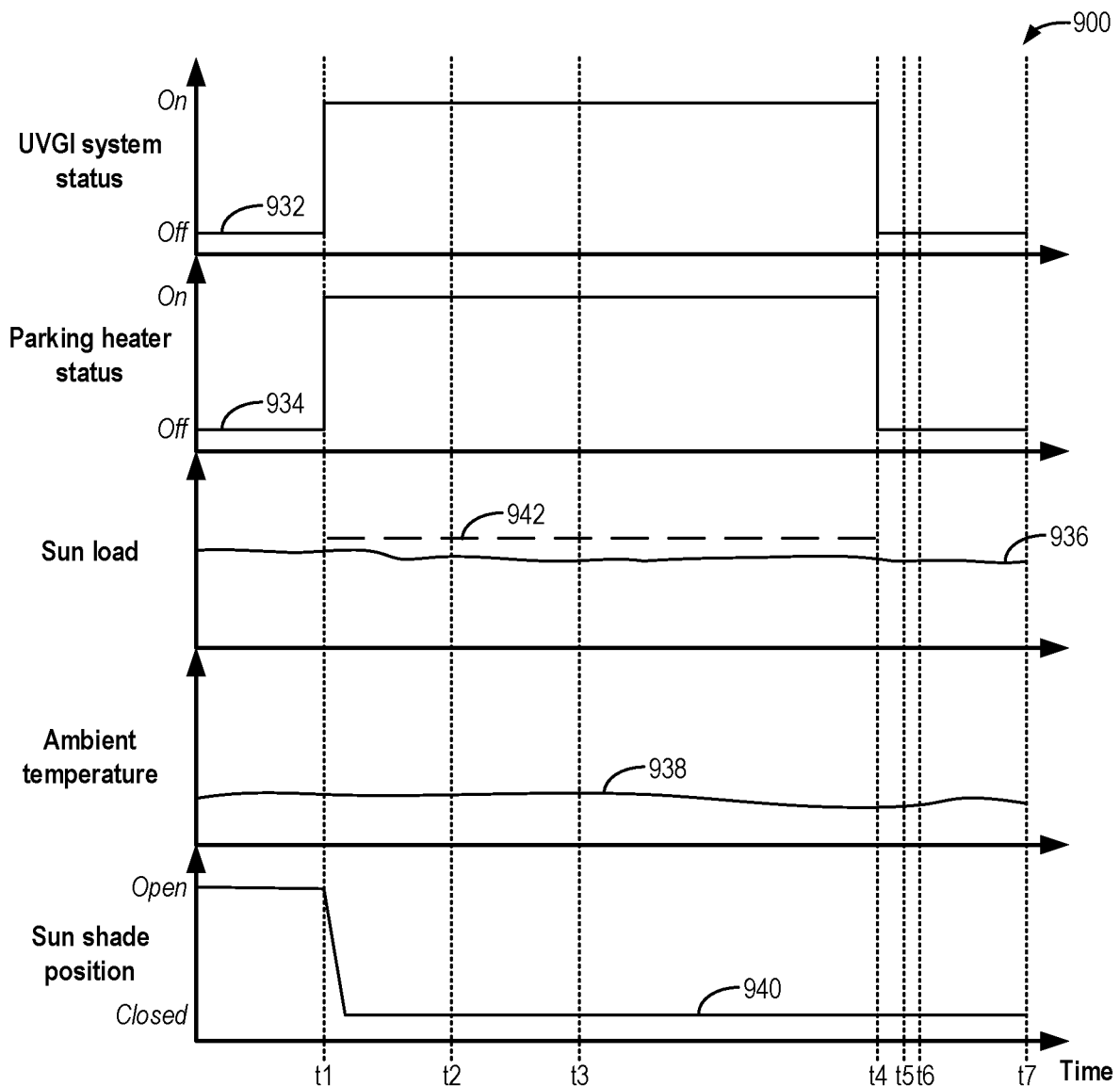

Turning now to FIGS. 9A and 9B, a second example timeline 900 for adjusting powertrain and HVAC system operation to operate in a vehicle sanitizing mode is shown. Engine speed is shown in a plot 902, a cabin temperature is shown in a plot 904, a blower speed is shown in a plot 906, an air-conditioning compressor status is shown in a plot 908, an engine cooling fan status is shown in a plot 910, an air inlet door position is shown in a plot 912, a blend door position is shown in a lot 914, an air flow delivery status of a vent mode is shown in a short-dashed plot 916, an airflow delivery status of a floor mode is shown in a dotted plot 918, an airflow delivery status of a panel mode is shown in a long-dashed plot 920, a UVGI system status is shown in a plot 932, a parking heater status is shown in a plot 934, a sun load is shown in a plot 936, an ambient temperature is shown in a plot 938, and a sun shade position is shown in a plot 940.

For all of the above, the horizontal axis represents time, with time increasing along the horizontal axis from left to right. The vertical axis represents each labeled parameter. For plots 902, 904, 936, and 938, a magnitude of the labeled parameter increases along the vertical axis from bottom to top. For plot 906, the vertical axis shows the blower speed setting as "off" (e.g., a speed of zero), "low," "medium," or "high." For plots 908, 910, 932, and 934, the vertical axis indicates whether the corresponding component is "on" (e.g., active) or "off" (e.g., inactive). For plot 912, the vertical axis shows the air inlet door position ranging from a recirculated air position ("recirc."), at which air is recirculated through the HVAC system from the vehicle cabin, and a fresh air position ("fresh"), at which air is drawn into the HVAC system from outside the vehicle. For plot 914, the blend door position is shown ranging from a hot position ("hot"), at which only hot air is provided to the vehicle cabin, and a cold position ("cold"), at which only cold air is provided to the vehicle cabin. For plots 916, 918, and 920, the vertical axis shows whether the corresponding air flow delivery mode is "on" (e.g., providing air flow to the cabin) or "off" (e.g., not providing air flow to the cabin). For plot 940, the position of the sun shade is shown with respect to a fully open position ("open") and a fully closed position ("closed").

Further, an engine idle speed setting is shown by a dashed line 922, a nominal climate control temperature range is shown by dashed lines 924 and 926 (dashed line 924 defining an upper threshold temperature of the nominal climate control temperature range and dashed line 926 defining a lower threshold temperature of the nominal climate control temperature range), a sanitization threshold temperature is shown by a dashed line 928, a cooldown threshold temperature is shown by a dashed line 930, and a sun load threshold is shown by a dashed line 942. Note that timeline 900 gives one illustrative example of the sanitization threshold temperature and the cooldown threshold temperature relative to the nominal climate control temperature range. In other examples, the cooldown threshold temperature may be higher than the upper threshold temperature of the nominal climate control temperature range, for example. However, it may be understood that the nominal climate control temperature range may not overlap with the sanitization threshold temperature.

Prior to time t1, the vehicle is operated in a nominal climate control mode. The engine is idling, with the engine speed (plot 902) at a lower engine idle speed setting (dashed line 922). Further, the engine cooling fan is on and operating at a non-zero speed (plot 910). The cabin temperature (plot 904) is maintained within the nominal climate control temperature range according to inputs received from a vehicle operator. In the example shown, based on the relatively low ambient temperature (plot 938) and the received inputs, the blower is operated at the medium speed setting (plot 906), the AC compressor is off (plot 908), the air inlet door is in the recirculated air position in order to provide recirculated air (plot 912), the blend door is positioned to provide fully hot air (plot 914), and the air flow is delivered to the cabin via panels. Thus, the panel mode is on (plot 920), while the floor more (plot 918) and the vent mode (plot 916) are off. Further, the sun shade is positioned at a fully open position (plot 940) to maximize an amount of light transmitted through a roof window, such as due to the moderately high sun load (plot 936). Further still, the parking heater is off, as auxiliary heating is not used to warm the engine and cabin.

At time t1, the vehicle enters the vehicle sanitizing mode in response to an input received from the vehicle operator. A state machine of the vehicle sanitizing mode is transitioned to a heating phase, and the powertrain and HVAC system are operated with the corresponding heating phase settings. In particular, the engine idle speed setting is increased (dashed line 922), and engine operation is adjusted to increase the engine speed to the higher engine idle speed setting (plot 902). For example, additional air and fuel are supplied to the engine to increase the engine speed. Further, the engine cooling fan is commanded off (plot 910) in order to decrease engine cooling, thereby increasing an engine coolant temperature to a higher engine coolant temperature set-point, and thus, an amount of heat transferred to air via a heater core of the HVAC system. The blend door is maintained in the hot position (plot 914) so that no cold air is included in the air flow provided to the cabin, and the air-conditioning compressor is maintained off (plot 908). Further, the blower speed is increased to the high (e.g., maximum) setting (plot 906), and air flow is provided to the cabin via the floor mode only. That is, the floor mode is turned on (plot 918), the vent mode is maintained off (plot 916), and the panel mode is turned off (plot 920). As a result the cabin temperature begins to increase (plot 904).

Further still, at time t1, the UVGI system is activated (plot 932) to irradiate cabin surfaces with germicidal UV light, and the parking heater is turned on to provide auxiliary heat (plot 934). The control system determines the threshold sun load (dashed line 942) based on the ambient temperature (plot 938). In the example of timeline 900, the threshold sun load is set to be relatively high due to the lower ambient temperature (plot 938). For example, even though it is relatively bright outside, the decreased thermal insulation at the roof window while the sun shade is open is weighed against the low ambient temperature. Because the sun load (plot 936) is less than the threshold sun load, the sun shade is adjusted to the fully closed position (plot 940) in order to decrease an amount of heat transferred from the cabin to the ambient environment via the roof window.

At time t2, the engine coolant temperature reaches a threshold temperature (not shown). In response, the air inlet door position is adjusted from the recirculated air position to the fresh air position (plot 912).

At time t3, the cabin temperature (plot 904) reaches the sanitization threshold temperature (dashed line 928). In response, the state machine is transitioned to a maintain phase, which tracks a duration of time at which the cabin temperature (plot 904) remains above the sanitization threshold temperature (dashed line 928). As shown, the sanitization threshold temperature is a maximum threshold temperature used for the cabin temperature.

At time t4, the duration tracked by the maintain phase reaches a threshold duration, and heating is considered complete. Further, vehicle sanitization is considered successful, and the state machine transitions to a cooldown (or success) phase. To transition to the cooldown phase, the engine idle speed setting is decreased to the nominal idle speed setting used prior to entering the vehicle heating mode (dashed line 922), and the engine speed is decreased accordingly (plot 902). Further, the engine cooling fan is turned on (plot 910). The UVGI system (plot 932) and the parking heater (plot 934) are both deactivated. As such, the UVGI system will no longer irradiate the cabin surfaces, and the parking heater will no longer supply auxiliary heat to the cabin and engine.

At the beginning of the cooldown phase (e.g., beginning at time t4), the blend door remains fully at the hot position (plot 912), the air inlet door remains at the fresh air position (plot 912), the blower speed remains at the high setting (plot 906), and the air flow continues to be provided to the cabin only via the floor mode (plot 918). However, because additional heat is no longer generated by the engine, the cabin temperature begins to decrease (plot 904).

At time t5, which occurs after a first amount of time of operating in the cooldown phase, the blend door position is adjusted to be halfway between the hot position and the cold position (plot 914). Further, at time t6, which occurs after a second amount of time of operating in the cooldown phase, the blend door position is further adjusted to the cold position (plot 914), and the air-conditioning compressor is turned on (plot 908). Further, the panel mode is turned on (plot 920) so that air flow is provided to the cabin via both the panel mode and the floor mode (and not the vent mode).

At time t7, the cabin temperature (plot 904) decreases to the cooldown threshold temperature (dashed line 930). As a result, the vehicle sanitizing mode is considered to be completed, and the state machine transitions to an inactive state. Thus, following time t7, the HVAC system is operated in the nominal climate control mode responsive to inputs from the vehicle operator. In some examples, the sun shade position may be adjusted back to the position it was in prior to operating in the vehicle sanitizing mode (e.g., the fully open sun shade position prior to time t1.

Figure 10:
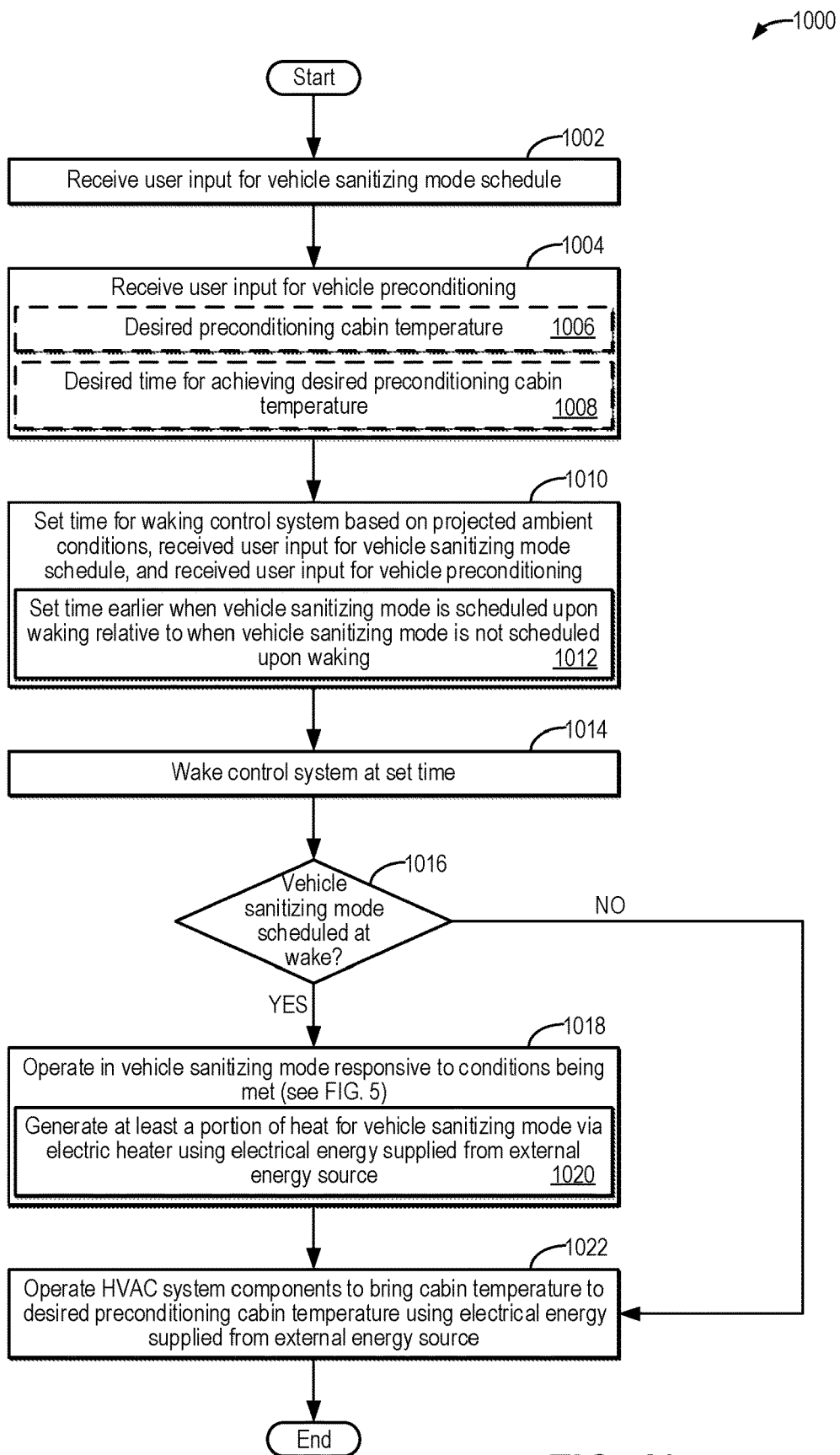
FIG. 10 shows a flow chart of an example method for scheduling and performing vehicle sanitization and preconditioning.

Next, FIG. 10 shows an example method 1000 for preconditioning a plug-in EV or HEV. The vehicle may be vehicle 200 shown in FIG. 2 and may be propelled by vehicle propulsion system 100 of FIG. 1, for example, that selectively receives electrical power from an external power source (e.g., external power source 180 of FIG. 1). Further, the vehicle may include an HVAC system, such as HVAC system 220 shown in FIGS. 2 and 3, which may be used to provide heat to a vehicle cabin. Instructions for carrying out method 1000 and the rest of the methods included herein may be executed by one or more control modules or controllers of a control system (e.g., control system 190 of FIGS. 1 and 4) based on instructions stored on one or more memories of the control system and in conjunction with signals received from sensors of the vehicle system, such as the sensors described above with reference to FIGS. 1-2. The control system may employ actuators of the vehicle system to adjust vehicle system operation according to the methods described below.

At 1002, method 1000 includes receiving user input for a vehicle sanitizing mode schedule. The user input may be received via a user interface communicatively coupled with the control system, such as a HMI of the vehicle (e.g., HMI

196 of FIG. 2) or a remote device (e.g., smartphone 295 of FIG. 2). The user input for the vehicle sanitizing mode schedule may include the user setting a frequency for operating in the vehicle sanitizing mode and performing a sanitizing routine, such as the routine described above with respect to FIG. 5, a time of day for performing the sanitizing routine, a number of driven miles or vehicle trips between each execution of the sanitizing routine, etc. As one example, the user input may specify to perform the sanitizing routine once a week before 9:00 am while the vehicle electrically coupled to the external power source.

At 1004, method 1000 includes receiving user input for vehicle preconditioning. The user input for the vehicle precondition may include a desired preconditioning cabin temperature, as indicated at 1006. The desired preconditioning cabin temperature refers to a user-specified cabin temperature set-point to achieve for climate comfort via the preconditioning, which occurs before the user operates the vehicle. The user input for the vehicle preconditioning may further include a desired time for achieving the desired preconditioning cabin temperature, as indicated at 1008. For example, the user may specify a pre-set time for the preconditioning to be completed. The pre-set time may be a single time (e.g., 8:30 am the following day) or a schedule of times (e.g., 8:30 am every weekday).

Additionally or alternatively, the control system may automatically schedule the preconditioning responsive to an anticipation of a vehicle start while the vehicle is coupled to the external power source, such as according to learned/predicted driving routes (e.g., routes that are frequented according to a daily, weekly, or monthly schedule within a common time of day and day of the week). Further, the controller may automatically determine the desired preconditioning cabin temperature according to learned/predicted climate control data, such as based on an average requested cabin temperature. In such examples, the received user input may include the user activating the automatic preconditioning so that the preconditioning is automatically performed (e.g., without additional user input) according to the learned driving routes and cabin temperature or deactivating the automatic preconditioning so that the preconditioning is not automatically performed.

At 1010, method 1000 includes setting a time for waking the control system based on projected ambient conditions, the received user input for the vehicle sanitizing mode schedule, and the received user input for the vehicle preconditioning. For example, the projected ambient conditions may be determined via a weather report, which may be accessed by the control system via the Internet or other communication network. As one example, the control system may input one or more of the projected ambient conditions, the received user input for the vehicle sanitizing mode schedule, and the received user input for the vehicle preconditioning into a look-up table, algorithm, or model, which may output the time for waking the control system.

Further, setting the time for waking the control system includes setting the time earlier when the vehicle sanitizing mode is scheduled upon waking relative to when the vehicle sanitizing mode is not scheduled upon waking, as indicated at 1012. Because the vehicle sanitizing mode includes heating the cabin to a temperature that is higher than that used for climate control and holding the cabin temperature at the higher temperature for a duration, setting the time earlier when the vehicle sanitizing mode is scheduled provides time for both performing the sanitizing routine and cooling the cabin to the desired preconditioning cabin temperature. Thus, the control system may estimate and account for an amount of time it is expected to take to both perform the sanitizing routine and cool the cabin to the desired preconditioning cabin temperature in setting the time for waking the control system.

Setting the time for waking the control system may include both determining the time, as described above, and setting a timer or alarm for the determined time. Once the time for waking the control system is set, the timer or alarm may begin a countdown to the set time (or begin counting up from zero to the set time). Alternatively, the set time may be given as global real time, which may be tracked by timer or alarm.

At 1014, method 1000 includes waking the control system at the set time. As one example, the control system may be transitioned to a lower power sleep mode in between setting the time for waking the control system and the timer or alarm elapsing. As such, the control system may be returned to a full power awake mode upon the timer or alarm elapsing. However, it may be understood that in examples where the control system is already in the awake mode at the set time, the control system is maintained in the awake mode and prevented from transitioning to the sleep mode. Further, it may be understood that the timer or alarm may remain powered while the control system is in the sleep mode in order to compare a current time with the set time, count up from zero to the set time, or count down to zero. The timer or alarm may elapse responsive to the current time reaching the set time, for example, causing the control system to transition back to the awake mode and/or execute the scheduled preconditioning.

At 1016, it is determined if the vehicle sanitizing mode is scheduled at the wake. For example, preconditioning may be scheduled five times a week, whereas the vehicle sanitizing mode may be scheduled once a week. Thus, in some examples, the control system may wake to perform only preconditioning for cabin comfort and battery optimization. If the vehicle sanitizing mode is not scheduled to occur at the current wake, method 1000 proceeds to 1022 and includes operating the HVAC system components to bring the cabin temperature to the desired preconditioning cabin temperature using electrical energy supplied from the external energy source. For example, the control system may operate heating and/or cooling components of the HVAC system depending on a current cabin temperature relative to the desired preconditioning cabin temperature.

As one example, the control system may determine the settings of the heating and cooling components of the HVAC system by inputting a difference between the current cabin temperature and the desired preconditioning cabin temperature into a look-up table, algorithm, or map. The control system may determine, for example, a ratio of hot air to cold air to be generated by HVAC system heating and cooling elements respectively, a setting for activating the electric heater, a setting for an AC compressor, and/or a ratio of fresh air to recirculated air to be mixed into an air flow provided to the cabin. For example, the control system may determine a position of a blend door and a position of an air inlet door accordingly. The control system may further determine a rate and direction of air flow to provide to the cabin to bring the current cabin temperature to the desired preconditioning cabin temperature. For example, the control system determine a speed of a blower and a position of one or more delivery doors, and then actuate the blower at the determined speed and adjust the one or more delivery doors to the determined position(s). Method 1000 may then end.

If instead the vehicle sanitizing mode is scheduled to occur at the current wake, method 1000 proceeds to 1018 and includes operating in the vehicle sanitizing mode responsive to conditions being met, as described above with respect to FIG. 5. For example, the control system may perform all or parts of method 500 of FIG. 5 at 1018. Briefly, the vehicle sanitizing mode includes operating the HVAC system in a heating cycle, a maintain cycle, and a cooldown cycle. The heating cycle comprises raising the temperature of the cabin to a maximum threshold temperature that is greater than the desired preconditioning cabin temperature, the maintain cycle comprises maintaining the temperature of the cabin at or above the maximum threshold temperature for a threshold duration, and the cooldown cycle comprises reducing the temperature of the cabin to a lower threshold temperature.

In particular, since the vehicle is receiving electrical energy from the external power source, the method at 1018 includes generating at least a portion of the heat for the vehicle sanitizing mode (e.g., for the heating cycle and the maintain cycle) via the electric heater using electrical energy supplied from the external energy source, as indicated at 1020. For example, when the vehicle is an EV without a fuel-operated parking heater, all of the heat for the vehicle sanitizing mode may be generated via the electric heater. As another example, when the vehicle is an EV that includes a fuel-operated parking heater, a first portion of the heat for operating in the vehicle sanitizing mode may be generated by the electric heater, while a second, remaining portion may be generated by the fuel-operated parking heater, such as when supplementing the electric heater with the fuel-operated parking heater increases the cabin temperature more quickly and/or the electric heater alone is unable to reach a sanitization temperature (e.g., the first threshold temperature described above at 514 of FIG. 5). When the vehicle is a HEV, a first portion of the heat for operating in the vehicle sanitizing mode may be generated by the electric heater, while a second, remaining portion may be generated by the engine, such as when supplementing the electric heater with heat from the engine increases the cabin temperature more quickly and/or the electric heater alone is unable to reach the sanitization temperature. In some examples, the control system may prioritize providing heat via the electric heater in order to advantageously reduce fuel and battery depletion while the vehicle is receiving electrical energy from the external power source.

During the cooldown cycle, the electric heater is deactivated (along with other heating components of the HVAC system) and an air conditioning compressor is activated, as described above at 520 of FIG. 5. The air conditioning compressor may be powered via the electrical energy supplied from the external power source, for example.

At 1022, method 1022 includes operating the HVAC system components to bring the cabin temperature to the desired preconditioning cabin temperature using electrical energy supplied from the external energy source, as described above. For example, the desired preconditioning cabin temperature may be lower than the lower threshold temperature of the cooldown cycle. In such an example, the cooling components of the HVAC system may be operated to continue to decrease the cabin temperature (e.g., as measured by a cabin temperature sensor). In this way, the cabin temperature may be brought to the desired preconditioning cabin temperature following operating in the vehicle sanitizing mode, enabling both vehicle cleaning and preconditioning to be performed while the vehicle is receiving electrical energy from the external power source. As a result, the vehicle may be readied for a drive with minimal input from the vehicle operator and with reduced downtime relative to separately performing preconditioning and the sanitizing routine.

In this way, interior vehicle surfaces may be sanitized without using chemical agents and by advantageously using components already included in the vehicle. By operating in a vehicle sanitizing mode to command powertrain and/or HVAC system components to generate and direct hot air to the interior vehicle surfaces, heat-sensitive microbes existing on the interior vehicle surfaces may be killed or deactivated. Further, by adjusting powertrain and/or HVAC system settings based on vehicle climate conditions, such as an ambient temperature and a sun load of the vehicle, an amount fuel and/or electric energy consumed while operating in the vehicle sanitizing mode may be reduced. By using a combination of hot air and UV light to decontaminate the interior vehicle surface, hard-to-reach areas may be more easily and more effectively decontaminated than when chemical sanitizers are used. Overall, pathogen transmission from the interior vehicle surfaces to humans may be reduced.

The technical effect of directing UV germicidal irradiation toward vehicle surfaces is that the vehicle surfaces may be decontaminated.

In one example, a method comprises: responsive to receiving a request for cleaning an interior of a vehicle, activating an ultraviolet germicidal irradiation (UVGI) system and operating a heating, ventilation, and air-conditioning (HVAC) system to heat the interior above an upper threshold temperature for a first threshold duration. In a first example of the method, the UVGI system includes a plurality of ultraviolet (UV) light sources directed at a plurality of surfaces of the interior of the vehicle, and activating the UVGI system includes emitting light from the UV light sources. In a second example of the method, optionally including the first example, the light emitted from the UV light sources is within a short-wavelength UV light range. In a third example of the method, optionally including one or both of the first and second examples, the light emitted from the UV light sources includes light having a wavelength between 100 and 280 nanometers. In a fourth example of the method, optionally including any or all of the first through third examples, activating the UVGI system and operating the HVAC system to heat the interior above the upper threshold temperature for the first threshold duration is further responsive to an indication the vehicle is unoccupied, an indication the vehicle is parked, and an indication vehicle doors and windows are closed, and wherein a temperature of hot air provided by the HVAC system to the interior is greater than when provided for climate control. In a fifth example of the method, optionally including any of all of the first through fourth examples the HVAC system includes a blower configured to generate air flow through the HVAC system, a heating component configured to receive the air flow from the blower, delivery ducting fluidic ally coupling the heating component to the interior, and a blend door configured to adjust a ratio of hot air to cold air provided to the delivery ducting, and operating the HVAC system to heat the interior above the upper threshold temperature for the first threshold duration comprises: operating the blower at maximum speed; generating the hot air at the heating component; flowing the hot air from the heating component to the interior via the delivery ducting; setting a position of the blend door to maximize the ratio of the hot air to the cold air provided to the delivery ducting; and operating the delivery ducting in a floor mode. In a sixth example of the method, optionally including any of all of the first through fifth examples, the method further comprises: responsive to a temperature of the interior being above the upper threshold temperature for the first threshold duration, deactivating the UVGI system and operating the HVAC system to gradually reduce the temperature of the interior until one of a lower threshold temperature and a second threshold duration is reached. In a seventh example of the method, optionally including any of all of the first through sixth examples, operating the HVAC system to gradually reduce the temperature of the interior comprises: sequentially adjusting the position of the blend door to decrease the ratio of the hot air to the cold air provided to the delivery ducting over time, operating the delivery ducting in a panel mode in addition to the floor mode after a pre-determined duration has elapsed while operating the HVAC system to gradually reduce the temperature of the interior, and activating an air-conditioning compressor after the pre-determined duration has elapsed. In an eighth example of the method, optionally including any of all of the first through seventh examples, the heating component is a heater core that receives hot coolant from an engine, and the method further comprises: responsive to receiving the request for cleaning the interior of the vehicle, increasing an idle speed set-point of the engine and turning off an engine cooling fan. In a ninth example of the method, optionally including any of all of the first through eighth examples, the HVAC system further includes an air inlet door configured to adjust a ratio of fresh air to recirculated air provided to the HVAC system, and operating the HVAC system to heat the interior above the upper threshold temperature for the first threshold duration further comprises: positioning the air inlet door in a recirculated air position until a temperature of the hot coolant increases above a threshold coolant temperature, and then adjusting the air inlet door to a fresh air position. In a tenth example of the method, optionally including the any of all of first through ninth examples, the method further comprises: adjusting one or both of the upper threshold temperature and the first threshold duration based on a humidity of the interior of the vehicle, including decreasing one or both of the upper threshold temperature and decreasing the first threshold duration as the humidity of the interior of the vehicle increases.

As another example, a method comprises: in a first mode, operating a powertrain and a heating, ventilation, and air conditioning (HVAC) system to provide air of a maximum threshold temperature to a vehicle cabin and operating an ultraviolet germicidal irradiation (UVGI) system; and in a second mode, operating the powertrain and the HVAC system to provide air within a threshold temperature range to the vehicle cabin, the threshold temperature range including temperatures lower than the maximum threshold temperature, and not operating the UVGI system. In a first example of the method, operating the powertrain and the HVAC system to provide the air of the maximum threshold temperature to the vehicle cabin includes increasing an idle speed of an engine above a default idle speed used while operating the powertrain and the HVAC system in the second mode, and wherein operating the UVGI system includes supplying electrical power to the UVGI system to power a plurality of ultraviolet (UV) lights positioned in the vehicle cabin. In a second example of the method, optionally including the first example, the first mode comprises a heating cycle, a maintain cycle, and a cooldown cycle, each of the heating cycle, the maintain cycle, and the cooldown cycle including powertrain and HVAC system settings that are independent of climate control inputs received from a climate control interface, and the second mode adjusts the powertrain and HVAC system settings based on the climate control inputs received from the climate control interface. In a third example of the method, optionally including one or both of the first and second examples, the first mode does not occur while the vehicle cabin is occupied, and the second mode occurs while the vehicle cabin is occupied. In a fourth example of the method, optionally including any of all of the first through third examples, the second mode is a default mode, and the first mode is triggered responsive to receiving a pre-determined input sequence.

In another example, a vehicle system comprises: a powertrain; a heating, ventilation, and air-conditioning (HVAC) system; a cabin; one or more ultraviolet (UV) light sources positioned within the cabin; a control system, including a plurality of control modules communicatively coupled over a controller area network; and computer-readable instructions stored in non-transitory memory of one or more of the plurality of control modules that, when executed, cause the control system to: increase an amount of heat generated by the powertrain and transferred to air provided to the cabin via the HVAC system while operating in a vehicle cleaning mode relative to a nominal climate control mode; activate the one or more UV light sources to emit UV light while operating in the vehicle cleaning mode; and maintain the one or more UV light sources deactivated while operating in the nominal climate control mode. In a first example of the system, the vehicle cleaning mode includes one or more of sanitizing and decontaminating, wherein the powertrain includes an engine and an engine cooling system, and to increase the amount of heat generated by the powertrain and provided to the cabin via the HVAC system while operating in the vehicle cleaning mode, the computer-readable instructions, when executed, cause the control system to: increase an idle speed of the engine relative to the nominal climate control mode while operating in a heating portion of the vehicle cleaning mode, and turn off an engine cooling fan of the engine cooling system while operating in the heating portion of the vehicle cleaning mode. In a second example of the system, optionally including the first example, the powertrain includes an electric motor and the HVAC system includes an electric heater, and to increase the amount of heat generated by the powertrain and provided to the cabin via the HVAC system while operating in the vehicle cleaning mode, the computer-readable instructions, when executed, cause the control system to: engage the electric motor against brakes of the vehicle during a heating portion of the vehicle cleaning mode, and activate the electric heater during the heating portion of the vehicle cleaning mode. In a third example of the system, optionally including one or both of the first and second examples, the HVAC system includes a blower, a heating component positioned to receive air flow from the blower, an air-conditioning evaporator positioned to receive air flow from the blower, an air-conditioning compressor for compressing a refrigerant evaporated by the air-conditioning evaporator, a blend door adjustable between a hot position that maximizes air flow from the heating component and a cold position that maximizes air flow from the air-conditioning evaporator, a floor mode delivery duct, a vent mode delivery duct, and a panel mode delivery duct, and to increase the amount of heat generated by the powertrain and provided to the cabin via the HVAC system while operating in the vehicle cleaning mode, the computer-readable instructions, when executed, cause the control system to: operate the blower at maximum speed, turn off the air-conditioning compressor, adjust the blend door to the hot position, open the floor mode delivery duct, close the vent mode delivery duct, and close the panel mode delivery duct.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations, and/or functions may be repeatedly performed depending on the particular strategy being used. Further, the described actions, operations, and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, 1-4, 1-6, V-12, opposed 4, and other engine types. Moreover, unless explicitly stated to the contrary, the terms "first," "second," "third," and the like are not intended to denote any order, position, quantity, or importance, but rather are used merely as labels to distinguish one element from another. The subject matter of the present disclosure includes all novel and non-obvious combinations and sub-combinations of the various systems and configurations, and other features, functions, and/or properties disclosed herein.

As used herein, the term "approximately" is construed to mean plus or minus five percent of the range unless otherwise specified.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method, comprising:
responsive to receiving a request for cleaning an interior of a vehicle, activating an ultraviolet germicidal irradiation (UVGI) system, operating a heating, ventilation, and air-conditioning (HVAC) system, and further operating one or more heated surfaces that include electronically controlled heating elements, radiant panels, and/or fibers, during heating of the interior, to heat the interior above an upper threshold temperature for a first threshold duration; wherein the HVAC system includes a blower configured to generate air flow through the HVAC system, a heating component configured to receive the air flow from the blower, delivery ducting fluidically coupling the heating component to the interior, and a blend door configured to adjust a ratio of hot air to cold air provided to the delivery ducting, and operating the HVAC system to heat the interior above the upper threshold temperature for the first threshold duration comprises:
operating the blower at maximum speed;
generating the hot air at the heating component;
flowing the hot air from the heating component to the interior via the delivery ducting;
setting a position of the blend door to maximize the ratio of the hot air to the cold air provided to the delivery ducting; and
operating the delivery ducting in a floor mode.

2. The method of claim 1, wherein the UVGI system includes a plurality of ultraviolet (UV) light sources directed at a plurality of surfaces of the interior of the vehicle, and activating the UVGI system includes emitting light from the plurality of UV light sources, and wherein the one or more heated surfaces include heated seats and a heated steering wheel.

3. The method of claim 1, wherein the HVAC system communicates with a powertrain control module (PCM) to increase an engine idle speed and switch off an engine cooling fan to increase a temperature of engine coolant provided to the HVAC system.

4. The method of claim 1, further comprising adjusting a position of a sun shade during the operating of the HVAC system to heat the interior, including closing the sun shade responsive to ambient temperature below a threshold ambient temperature.

5. The method of claim 1, wherein activating the UVGI system and operating the HVAC system to heat the interior above the upper threshold temperature for the first threshold duration is further responsive to an indication the vehicle is unoccupied, an indication the vehicle is parked, and an indication vehicle doors and windows are closed, and wherein a temperature of hot air provided by the HVAC system to the interior is greater than when provided for climate control.

6. The method of claim 1, further comprising:
responsive to a temperature of the interior being above the upper threshold temperature for the first threshold duration, deactivating the UVGI system and operating the HVAC system to gradually reduce the temperature of the interior until one of a lower threshold temperature and a second threshold duration is reached.

7. The method of claim 6, wherein operating the HVAC system to gradually reduce the temperature of the interior comprises:
sequentially adjusting the position of the blend door to decrease the ratio of the hot air to the cold air provided to the delivery ducting over time;
operating the delivery ducting in a panel mode in addition to the floor mode after a pre-determined duration has elapsed while operating the HVAC system to gradually reduce the temperature of the interior; and
activating an air-conditioning compressor after the pre-determined duration has elapsed.

8. The method of claim 1, wherein the heating component is a heater core that receives hot coolant from an engine, and the method further comprises:
responsive to receiving the request for cleaning the interior of the vehicle, increasing an idle speed set-point of the engine and turning off an engine cooling fan.

9. The method of claim 8, wherein the HVAC system further includes an air inlet door configured to adjust a ratio of fresh air to recirculated air provided to the HVAC system, and operating the HVAC system to heat the interior above the upper threshold temperature for the first threshold duration further comprises:
positioning the air inlet door in a recirculated air position until a temperature of the hot coolant increases above a threshold coolant temperature, and then adjusting the air inlet door to a fresh air position.

10. The method of claim 1, further comprising:
adjusting one or both of the upper threshold temperature and the first threshold duration based on a humidity of the interior of the vehicle, including decreasing one or both of the upper threshold temperature and the first threshold duration as the humidity of the interior of the vehicle increases.

11. A method, comprising:
in a first mode, operating a powertrain and a heating, ventilation, and air conditioning (HVAC) system to provide air of a maximum threshold temperature to a vehicle cabin, operating an ultraviolet germicidal irradiation (UVGI) system, operating one or more heated surfaces that include electronically controlled heating elements, closing a sun shade responsive to a sun load threshold, wherein the sun load threshold is set based on ambient temperature to be relatively higher at lower ambient temperatures, increasing an engine idle speed, and switching off an engine cooling fan from an already running position even with engine coolant temperature increasing to a higher engine coolant temperature; and
in a second mode, operating the powertrain and the HVAC system to provide air within a threshold temperature range to the vehicle cabin, the threshold temperature range including temperatures lower than the maximum threshold temperature, and not operating the UVGI system.

12. The method of claim 11, wherein operating the powertrain and the HVAC system to provide the air of the maximum threshold temperature to the vehicle cabin includes increasing the engine idle speed above a default idle speed used while operating the powertrain and the HVAC system in the second mode, and wherein operating the UVGI system includes supplying electrical power to the UVGI system to power a plurality of ultraviolet (UV) lights positioned in the vehicle cabin.

13. The method of claim 11, wherein the first mode comprises a heating cycle, a maintain cycle, and a cooldown cycle, each of the heating cycle, the maintain cycle, and the cooldown cycle including powertrain and HVAC system settings that are independent of climate control inputs received from a climate control interface, and the second mode adjusts the powertrain and HVAC system settings based on the climate control inputs received from the climate control interface.

14. The method of claim 11, wherein the first mode does not occur while the vehicle cabin is occupied, and the second mode occurs while the vehicle cabin is occupied.

15. The method of claim 11, wherein the second mode is a default mode, and the first mode is triggered responsive to receiving a pre-determined input sequence.

16. A vehicle system, comprising:
a powertrain;
a heating, ventilation, and air-conditioning (HVAC) system;
a cabin;
one or more ultraviolet (UV) light sources positioned within the cabin;
a control system, including a plurality of control modules communicatively coupled over a controller area network; and
computer-readable instructions stored in non-transitory memory of one or more of the plurality of control modules that, when executed, cause the control system to:
increase an amount of heat generated by the powertrain and transferred to air provided to the cabin via the HVAC system while operating in a vehicle cleaning mode relative to a nominal climate control mode;
activate the one or more UV light sources to emit UV light while operating in the vehicle cleaning mode; and
maintain the one or more UV light sources deactivated while operating in the nominal climate control mode;
wherein the vehicle cleaning mode includes one or more of sanitizing and decontaminating, wherein the powertrain includes an engine and an engine cooling system, and to increase the amount of heat generated by the powertrain and provided to the cabin via the HVAC system while operating in the vehicle cleaning mode, the computer-readable instructions, when executed, cause the control system to:
increase an idle speed of the engine relative to the nominal climate control mode while operating in a heating portion of the vehicle cleaning mode; and
turn off an engine cooling fan of the engine cooling system while operating in the heating portion of the vehicle cleaning mode.

17. The vehicle system of claim 16, wherein the powertrain includes an electric motor and the HVAC system includes an electric heater, and to increase the amount of heat generated by the powertrain and provided to the cabin via the HVAC system while operating in the vehicle cleaning mode, the computer-readable instructions, when executed, cause the control system to:
engage the electric motor against brakes of the vehicle system during the heating portion of the vehicle cleaning mode; and
activate the electric heater during the heating portion of the vehicle cleaning mode.

18. The vehicle system of claim 16, wherein the HVAC system includes a blower, a heating component positioned to receive air flow from the blower, an air-conditioning evaporator positioned to receive air flow from the blower, an air-conditioning compressor for compressing a refrigerant evaporated by the air-conditioning evaporator, a blend door adjustable between a hot position that maximizes air flow from the heating component and a cold position that maximizes air flow from the air-conditioning evaporator, a floor mode delivery duct, a vent mode delivery duct, and a panel mode delivery duct, and to increase the amount of heat generated by the powertrain and provided to the cabin via the HVAC system while operating in the vehicle cleaning mode, the computer-readable instructions, when executed, cause the control system to:
operate the blower at maximum speed;
turn off the air-conditioning compressor;
adjust the blend door to the hot position;

open the floor mode delivery duct;
close the vent mode delivery duct; and
close the panel mode delivery duct.

\* \* \* \* \*